(12) United States Patent
Moeller et al.

(10) Patent No.: US 11,564,395 B2
(45) Date of Patent: Jan. 31, 2023

(54) FORMULATIONS WITH COLLOIDAL SILVER

(71) Applicant: AMERICAN SILVER, LLC, American Fork, UT (US)

(72) Inventors: Nathan R. Moeller, Highland, UT (US); Sheree M. Moeller, Highland, UT (US); Jerry S. Revelli, Highland, UT (US); Robert J. Holladay, Saratoga Springs, UT (US)

(73) Assignee: American Silver, LLC, American Fork, UT (US)

( * ) Notice: Subject to any disclaimer, the term of this patent is extended or adjusted under 35 U.S.C. 154(b) by 170 days.

(21) Appl. No.: 17/065,186

(22) Filed: Oct. 7, 2020

(65) Prior Publication Data
US 2021/0127682 A1    May 6, 2021

Related U.S. Application Data

(63) Continuation of application No. 15/753,289, filed as application No. PCT/US2016/047649 on Aug. 18, 2016, now abandoned.

(60) Provisional application No. 62/206,681, filed on Aug. 18, 2015.

(51) Int. Cl.
*A01N 59/16* (2006.01)
*A61K 8/04* (2006.01)
*A61K 8/19* (2006.01)
*A61K 8/27* (2006.01)
*A61K 31/60* (2006.01)
*A61K 33/38* (2006.01)
*A61Q 17/04* (2006.01)

(52) U.S. Cl.
CPC .............. *A01N 59/16* (2013.01); *A61K 8/044* (2013.01); *A61K 8/19* (2013.01); *A61K 8/27* (2013.01); *A61K 31/60* (2013.01); *A61K 33/38* (2013.01); *A61Q 17/04* (2013.01)

(58) Field of Classification Search
CPC . A61K 8/27; A61K 8/19; A61K 31/60; A61K 8/044; A61K 33/38; A01N 59/16; A01N 25/04; A01N 25/28; A01N 65/00; A61Q 17/04
See application file for complete search history.

(56) References Cited

U.S. PATENT DOCUMENTS

| 2006/0182813 A1* | 8/2006 | Holladay | A61K 47/10 424/618 |
| 2010/0136148 A1* | 6/2010 | Saint Victor | C11D 3/48 424/754 |

FOREIGN PATENT DOCUMENTS

WO    WO-2015057983 A1 *    4/2015    ............. A61K 33/38

* cited by examiner

*Primary Examiner* — Blessing M Fubara
(74) *Attorney, Agent, or Firm* — BioMed IP PLLC

(57) ABSTRACT

Colloidal silver particles are incorporated into emulsions and other compositions that find use, for example, as pharmaceutical and dermatological serums, creams, lotions and ointments.

13 Claims, No Drawings

FORMULATIONS WITH COLLOIDAL SILVER

CROSS-REFERENCE TO RELATED APPLICATION

This application is a continuation of U.S. application Ser. No. 15/753,289, filed Feb. 17, 2018, which is a national phase application under 35 U.S.C. § 371 of International Application No. PCT/US2016/047649, filed Aug. 18, 2016, which claims the benefit under 35 U.S.C. § 119(e) of U.S. Provisional Patent Application No. 62/206,681 filed Aug. 18, 2015, which each application is incorporated herein by reference in its entirety.

BACKGROUND OF THE INVENTION

The present disclosure relates generally to formulations comprising silver particles and the use thereof in, e.g., cosmetic, dermatologic and pharmaceutical formulations. For example, the present disclosure provides emulsions and formulations thereof, and in particular emulsions that contain silver particles, and formulations containing said emulsion in useful compositions such as cosmetic and dermatologic formulations.

SUMMARY OF THE INVENTION

In one aspect, the present disclosure provides emulsion-containing formulations, methods for making such formulations, and methods of using such formulations. Emulsions are currently found as part of many cosmetic, dermatologic and pharmaceutical formulations. The present disclosure provides improvements on these and other formulations that incorporate emulsions as described herein. The following are exemplary embodiments of the disclosure.

In one embodiment, the present disclosure provides a formulation comprising silver particles and an emulsion phase. Optionally, one or more of the following may further describe the formulation, where the following are exemplary only: it (the formulation) is in the form of a lotion, such as a skin lotion; it is in the form of a cream, such as a skin cream; it is in the form of an ointment, such as a healing ointment; it is in the form of a serum, such as an anti-aging serum, it is a cosmetic formulation; it is a dermatologic formulation; it is a therapeutic formulation; the silver particles range in size from 1-100 nanometers; the silver particles comprises a silver core surrounded by a multivalent silver oxide coating comprised of $Ag_4O_4$ molecules; the formulation has a concentration of silver particles of 1-100 ppm; the formulation has a concentration of silver particles of 10-40 ppm; the silver is characterized by particle size, and more than 50% of the silver particles have a maximum dimension of less than 0.015 micrometers; the formulation has a concentration of silver particles of between about 1 to about 100, or about 5 to about 40 parts per million, wherein said silver is in the form of a stable and colorless colloidal suspension of silver particles having an interior of metallic silver and an exterior surface of silver oxide, wherein at least 75% of the silver particles have diameters between 0.005 micrometers and 0.015 micrometers; the formulation comprises an oil, e.g., an oil selected from coconut oil, hemp seed oil, argan oil, shea butter, sunflower seed oil, neem oil, jojoba oil, and sweet almond oil; the formulation comprises a fatty acid, e.g., a fatty acid selected from C10-C28 fatty acids; the formulation comprises an emulsifying wax; the formulation comprises a surfactant; the formulation comprises hyaluronic acid; the formulation comprises a pH adjusting agent, e.g., a pH adjusting agent selected from ethanolamine, diethanolamine and triethanolamine. The formulation may provide one or more functional benefits, such as controlling, reducing or preventing acne, or providing lubrication as in a personal lubricant, as well as other functional benefits including those described herein.

In another embodiment, the present disclosure provides a method of preparing an emulsion, comprising combining an oil phase and a water phase, where the water phase comprises silver particles. Optionally, one or more of the following may further describe the method: the oil phase is added to the water phase; the water phase is added to the oil phase, the product from the method is in the form of a serum, for example, an anti-aging serum having anti-aging ingredients, the product from the method is in the form of a lotion, for example, a skin lotion; the product from the method is in the form of a cream, e.g., a skin cream; the product from the method is in the form of an ointment, e.g., a healing ointment; the product from the method is a cosmetic formulation; the product from the method is a dermatologic formulation; the product from the method is a therapeutic formulation; the silver particles range in size from 1 to 100 nanometers; the silver particles comprises a silver core surrounded by a multivalent silver oxide coating comprised of $Ag_4O_4$ molecules; the formulation has a concentration of silver particles of 1 to 100 ppm; the silver is characterized by particle size, and more than 50% of the silver particles have a maximum dimension of less than 0.015 micrometers; the product from the method has a concentration of silver particles of between about 5 parts per million and 40 parts per million, wherein said silver is in the form of a stable and colorless colloidal suspension of silver particles having an interior of metallic silver and an exterior surface of silver oxide, wherein at least 75% of the silver particles have diameters between 0.005 micrometers and 0.015 micrometers; the method includes using an oil selected from coconut oil, hemp seed oil, argan oil, shea butter, sunflower seed oil, neem oil, jojoba oil, and sweet almond oil; the method includes using a fatty acid, e.g., a fatty acid selected from C10-C28 fatty acids; the method includes using an emulsifying wax; the method includes using a surfactant; the method includes using hyaluronic acid (e.g., optionally having a molecular weight of less than 100,000 Daltons in order to avoid product discoloration); the method includes using a pH adjusting agent, e.g., a pH adjusting agent selected from ethanolamine, diethanolamine and triethanolamine.

In another embodiment, the present disclosure provides a method of using the silver particle-containing formulations disclosed herein. For example, the present disclosure provides a method of improving skin comprising applying to the skin an effective amount of a formulation as described herein, or prepared as described herein.

In another aspect, the present disclosure provides oil-free compositions that comprise silver particles and optionally at least one active ingredient. For example, the present disclosure provides a personal lubricant comprising silver particles, water and a thickening agent such as hydroxyethylcellulose (HEC). As another example, the present disclosure provides an acne treatment composition comprising silver particles, water, alcohol such as propylene glycol or polyethylene glycol, and an exfoliant such as salicylic acid or glycolic acid.

The present invention provides silver containing compositions that overcome problems associated with prior art silver containing compositions. In one embodiment the compositions contain silver in the +2 oxidation state, particularly in association with metallic silver, to provide potent antimicrobial properties. This high potency means that lower amounts of silver particles may be utilized in the preparation of the personal care formulations, thus avoiding undesirable side-reactions that can occur with silver, e.g., discoloration of the formulation, color instability, rheology instability, and oxidation of components of the formulation. This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the examples, and the claims.

DETAILED DESCRIPTION OF THE INVENTION

Briefly stated, in one embodiment the present invention provides emulsions that contain particulate silver. The emulsions may be formulated into a serum, a cream, a lotion, an ointment, etc. useful for any of, e.g., cosmetic, dermatologic or therapeutic purposes.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art. The headings used within this document are only being utilized to expedite its review by the reader, and should not be construed as limiting the invention or claims in any manner.

As used throughout this document, including the claims, the singular form "a", "an", and "the" include plural references unless indicated otherwise. For example, "a" surfactant includes one or more surfactants. As another example, "an" antibiotic refers to one or more antibiotics. Another example is that "a" natural plant extract includes one or more natural plant extracts. A composition that is disclosed to contain a named component or functional ingredient may, but need not, contain additional components or functional ingredients that may or may not be specifically identified herein. The terms composition and formulation are used interchangeably herein. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Emulsions

As used herein, an emulsion refers to a mixture that includes two immiscible phases, a hydrophilic (aqueous) phase and hydrophobic (oil) phase. In an emulsion, one of the two immiscible phases is in the form of small droplets that are dispersed in the other phase. For example, the emulsion may be an oil-in-water emulsion, in which case the emulsion includes the form of small droplets of oil dispersed throughout the water phase. Another example is a water-in-oil emulsion, in which case the emulsion includes the form of small droplets of water dispersed throughout the oil phase. The two immiscible phase are typically liquids. See, e.g., emulsions as described in PCT publication nos. WO15014573, WO14012918, WO14013194, and WO13180157, as well as U.S. patent application publication nos. US2015050321 and US2013302385 for further descriptions of emulsion.

In addition to oil-in-water emulsions and water-in-oil emulsions, exemplary emulsions of the present disclosure include water-in-silicone emulsions, silicone-in-water emulsions, water-in-oil-in-water, and oil-in-water-in-oil emulsions, and oil-in-water-in-silicone emulsions. The emulsion may be a microemulsion (see, e.g., EP2505180, US2014017185, US2011159104, CA2571906 and WO06136331) or a nanoemulsion (see, e.g., WO14197008 and U.S. Pat. No. 8,956,597). The emulsion may be a macroemulsion (see, e.g., US20140135406 and WO14143728). The emulsion may be a micro-scale heterogeneous emulsion (see, e.g., US2014335030). The emulsion may be a multiphase emulsion, for example a water-in-oil-in-water type, as disclosed in U.S. Pat. Nos. 4,254,105 and 4,960,764. The emulsion may comprise an aqueous dispersion of silicone elastomer particles (see, e.g., US 20150118320). The emulsion may be a post-foaming emulsion (see, e.g., US20150086500). The emulsion may be an inverse emulsion (see, e.g., WO14154700). These are examples of types of emulsions that are provided by the present disclosure. However, unlike the emulsions described in these documents, the emulsions of the present disclosure include particulate silver, which is typically present in the aqueous phase. Emulsions of the present disclosure may be prepared in analogy to the recipes provided in these listed documents, but using aqueous colloidal silver as described below, for some or all of the aqueous phase that is used in the recipes.

Colloidal Silver Particles

The term "colloidal silver" refers to a solution that can contain various concentrations of ionic silver compounds, silver particles, or silver compounds bound to proteins in water. In one embodiment, colloidal silver refers to particles which in whole or in part comprise silver, where the particles are suspended in an aqueous medium.

The total amount of colloidal silver in a composition may be between 1 ppm and 100 ppm. In optional embodiments, the content of colloidal silver in the composition is about 30±5 ppm, or 25±5 ppm, or 20±5 ppm, or 15±5 ppm, or 10±5 ppm. As the particles become smaller, a given concentration of particles will represent a larger number of particles. In addition, the total surface area for a given particle concentration will increase. Therefore, particle size and range of particle size may further characterize the compositions of the present invention. In further embodiments, the present disclosure provides that more than 50% of the particles have a maximum dimension less than 0.015 micrometers; or that more than 75% of the particles have a maximum dimension less than 0.015 micrometers; or that more than 90% of the particles have a maximum dimension less than 0.02 micrometers; or that more than 75% of the particles have a minimum dimension greater than 0.005 micrometers; or that more than 90% of the particles have a minimum dimension greater than 0.005 micrometers.

The particles may optionally be characterized in terms of valence of the silver. In one embodiment, the silver particles include both silver in the zero-valent state represented as [Ag(0)], i.e., metallic silver, and a coating of silver oxide in an oxidation state selected from Ag(I), Ag(II), and Ag(III). For example, the particles may have a coating of silver oxide, e.g., $Ag_2O$ or $Ag_4O_4$. In one embodiment, the silver oxide in the particles may be primarily in the form of $Ag_4O_4$, i.e., silver II oxide. In a molecule of this material two of the silver atoms are in the 1+ state (silver I) while the other two silver molecules are in the 3+ state (silver III). Under certain conditions these molecules can give rise to silver atoms or ions in the 2+ (silver II) state. Thus, the present disclosure provides silver particles comprising metallic silver and silver oxide, the silver oxide being selected from $Ag_2O$ and $Ag_4O_4$.

In one embodiment, any of the formulations of the present disclosure include silver in the +2 (also known as 2+ or Ag(II)) oxidation state. It has been surprisingly found that the selection of silver particles comprising silver in the +2 oxidation state affords a superior formulation as disclosed herein. Silver particles in the +2 oxidation state may be used in a low concentration that provides desirable benefits for the formulation, e.g., desirable anti-microbial benefits, and this low concentration does not cause undesirable effects or side-reactions that are observed at higher silver concentration. For example, at high silver concentration, silver can cause oxidation of some of the components of a formulation, notably components that are subject to oxidation. Components subject to oxidation include oils, particularly but not exclusively unsaturated oil, salts, acids such as hyaluronic acid and amino acids such a L-arginine, and fragrances that include oxidizable groups such as aldehyde groups, to name a few. In one embodiment, a formulation of the present disclosure contains silver particles comprising silver in the +2 oxidation state, the particles being present in the formulation within a stated concentration range having a minimum and maximum concentration, where the minimum concentration is selected from 0.01 ppm, or 0.02 ppm, or 0.03 ppm, or 0.04 ppm, or 0.05 ppm, or 0.06 ppm, or 0.07 ppm, or 0.08 ppm, or 0.09 ppm, or 0.1 ppm, or 0.2 ppm, or 0.3 ppm, or 0.4 ppm, or 0.5 ppm, or 0.6 ppm, or 0.7 ppm, or 0.8 ppm, or 0.9 ppm, or 1 ppm, or 2 ppm, or 3 ppm, or 4 ppm, or 5 ppm, or 6 ppm, or 7 ppm, or 8 ppm, or 9 ppm, or 10 ppm, and the maximum concentration is selected from 1,000 ppm, or 500 ppm, or 400 ppm, or 300 ppm, or 200 ppm, or 100 ppm, or 90 ppm, or 80 ppm, or 70 ppm, or 60 ppm, 50 ppm, or 40 ppm, or 30 ppm, or 25 ppm, or 20 ppm, or 15 ppm, or 10 ppm, where ppm has its standard meaning and refers to parts per million, i.e., weight parts of silver particles per one million weight parts of the formulation, e.g., 10 ppm refers to 10 grams of silver particles per every 1 million grams of formulation. Exemplary silver particle concentrations of 1-100 ppm, or 0.5-500 ppm, or 0.1-1,000 ppm, or less than 20 ppm, or less than 50 ppm, or 10-35 ppm are provided by the present invention, as well as concentrations within 1-100 ppm as mentioned previously. A benefit of using silver (II) at low concentration includes providing a product with a longer shelf life, e.g., providing a product that retains the desired performance benefit for a longer period of time, or providing a product that retains its consistency for a longer period of time, or providing a product that retains its original color for a longer period of time, since unwanted oxidation reactions that can shorten shelf life and/or damage the consistency of the product, and/or cause discoloration, are reduced. For example, the formulation may have at least about 10 ppm silver particles in order to provide good antimicrobial effectiveness but less than about 32 ppm silver particles in order to avoid discoloration of the formulation. Consistency in coloration and/or rheology over time may be measured while the formulation sits at room temperature, for example about 23° C., for a period of time, for example, 1 day, 2 days, 3 days, 4 days, 5 days, 6 days, 1 week, 2 weeks, 3 weeks, 4 weeks, 1 month, 2 months, 3 months, 4 months, 5 months or 6 months. Coloration and rheology may also be evaluated relative to target values. For example, if a white product is desired, and the silver concentration is too high, then a grey or yellowish product may result, indicating that too high of a concentration of silver is present in the formulation. In one embodiment, the silver particles used in the present formulations do not include any substantial amount of silver in the +1 oxidation state, but only has silver in the silver metal or +2 oxidation state, or if silver in the +1 oxidation state is present, it is present in a minor amount, i.e., less than the amount of silver present in the +2 oxidation state.

In one embodiment, the particles contain a thin multivalent silver oxide coating, built of numerous $Ag_4O_4$ molecules which surround a metallic nano-sized silver core. With the $Ag_4O_4$ coating, the nano silver particle is attracted to the surrounding water molecules, and as such, becomes part of the structure of the water. This makes the silver much more stable and bioavailable than other forms of silver.

Within optional embodiments of the invention these particles can range in size from 1-100 nanometers, or from 1-10 nanometers, or from 5-7 nanometers. Moreover, within preferred embodiments the particles are surrounded by a multivalent silver oxide coating comprised of $Ag_4O_4$ molecules.

In one embodiment, the compositions of the present disclosure include ionic silver, however in another embodiment, the compositions of the present disclosure do not include ionic silver, or else they contain minimal amounts of ionic silver. Ionic silver may be omitted from compositions of the present disclosure in order to avoid silver metabolism, which may lead to silver being bound up in the body and causing a skin condition known as Argyria, otherwise known as the blue man's syndrome.

In one embodiment, the compositions of the present disclosure include silver bound to protein, however in another embodiment, the compositions of the present disclosure do not include silver bound to protein, or else they contain minimal amounts of silver bound to protein. Protein-bound silver, also sometimes referred to as mild silver proteins, are another form of ionic silver. Because ionic forms of silver are not generally stable, they are sometimes bound to a protein to provide desired stability. However, as a consequence of binding with protein, the silver ion is less functional and useful than traditional ionic silver ions, and accordingly may be omitted from compositions of the present disclosure.

Exemplary aqueous compositions comprising colloidal silver particles are described in, and may be prepared by techniques disclosed in U.S. Pat. Nos. 6,214,299; 6,743,348; 7,135,195; and 8,535,728 as well as U.S Publication No. 2011/0262556. For example, the preparation of a composition comprising colloidal silver particles may utilize an electrochemical cell comprising electrodes. The process comprises the steps of: (a) placing a silver electrode in contact with a quantity of high purity water; (b) conveying electrical current through the silver electrode to thereby separate particles of silver from said silver electrode in a manner sufficient to cause production of suspended silver particles within the water; and (c) agitating the water during said production of suspended silver particles to thereby disperse the silver particles into a more uniform concentration within said water such that a higher quantity of colloidal silver particles can be produced per batch.

As another example, the preparation of a composition comprising colloidal silver particles may comprise the steps of: (a) establishing an electrical circuit comprising a current source, and a first conductor electrically connected to said current source and a second conductor electrically connected to said current source, wherein said first conductor is disposed spaced apart from said second conductor, and wherein at least one of the conductors is made of elemental silver; (b) closing the circuit by placing the first conductor and the second conductor in communication with a fluidic resistor; (c) operating the current source to supply alternating current simultaneously to the first conductor and the second conductor such that voltage is increasing and decreasing within the first and second conductors in alternating tandem to thereby cause silver particles to separate from the first electrode and enter the fluidic resistor and become disposed in suspension within said fluidic resistor; and (d) selectively adjusting the electrodes by moving them toward the fluidic resistor to compensate for decrease in electrode length due to gradual separation of silver particles therefrom to thereby prevent arcing from occurring between the electrodes and said fluidic resistor.

Other suitable colloidal silver particles and their preparation are described in, e.g., PCT Publication No. WO 2009/009143 and US Publication No. 2010/0187091.

In one embodiment, the colloidal silver particles are stable in essentially pure water without surfactants, etc. Additionally, or in another embodiment, the solution of colloidal silver particles is essentially colorless. In another embodiment, the colloidal silver particles are in saline. In another embodiment, the colloidal silver particles are in combination with electrolytes needed by a body, e.g., potassium and magnesium. In one embodiment, the colloidal silver particles are in saline, and the saline contains electrolytes. In one embodiment, the composition (e.g., aqueous composition, saline composition, etc.) contains colloidal silver particles at a lower concentration of 0.1 ppm, or 0.5 ppm, or 1 ppm, or 10 ppm, and at an upper concentration of 1,000 ppm, or 500 ppm, or 100 ppm. For example, concentrations of 1-100 ppm, or 0.5-500 ppm, or 0.1-1,000 ppm are provided by the present invention, as well as concentrations within 1-100 ppm as mentioned previously.

Composition Components

As stated above, the present invention provides emulsions which incorporate colloidal silver, preferably in particulate form, and which are particularly useful as cosmetic, dermatologic or therapeutic formulations, particularly in the form of creams, serums, lotions, ointments, and the like. The silver is typically utilized as an aqueous composition, e.g., the silver particles are dispersed and suspended in water, and such a composition can be used to provide the aqueous component of an emulsion, such as an oil-in-water or water-in-oil emulsion. In addition to the colloidal silver, which has been discussed above, the emulsions may be prepared from the following ingredients, where the identified ingredients are not the exclusive ingredients that may be present in the emulsion, but rather are options that may be employed in order to prepare the desired serum, lotion, cream, ointment etc. that contains an emulsion.

The compositions of the present disclosure may contain an emulsifying wax. Emulsifying waxes are a commonly used substance in a cosmetic formulations. Emulsifying wax is useful for the blending of creams, lotions and other fluid cosmetics which contain oil (a hydrophobic phase) and water (a hydrophilic phase). Emulsifying wax brings these two components, the oil phase and the water phase, into a single phase and maintains those incompatible materials as an emulsion phase. An emulsion is a system consisting of a liquid dispersed in an immiscible liquid, where immiscible means not compatible, i.e., not able to mix together to make a solution. Emulsifying wax assists in improving the consistency and texture of final products without leaving a greasy film on the outer skin after application. It also acts as a mild stabilizer and can impart thickness to a formulation, depending on how much wax is used. Emulsifying wax is recognized in the United States Pharmacopeia-National Formulary (USP-NF).

In one embodiment, this wax contain fats and esters, from either vegetable or animal sources. In one embodiment, the emulsifying wax is from plant sources. The wax may take the form of flakes or powder or shavings, for example. The following are exemplary emulsifying waxes: 1) emulsifying Wax NF (national formulary), typically used at a concentration of 3 and 6% of the total weight of the formulation, although more or less may be used; 2) ceteraryl alcohol/cetereth 20 may be used to prepare lotions, typically at a concentration of 2-6%, and may be used in combination with other emulsifying waxes. At higher concentrations, this material may be used for thicker, waxier creams; 3) cetearyl alcohol is a fatty alcohol derived from natural oils and fats (cetyl and stearyl alcohol) that can be used to thicken and stabilize formulations. Cetearyl alcohol may impart an emollient feel to the skin, and is typically used at a concentration of 1-25%; 4) glyceryl stearate is an emulsifier and an emulsion stabilizer. It is typically used in combination with a second emulsifier, such as POLYSORBATE 20 or CETEARETH 20. A typical concentration range of glyceryl stearate in a formulation is 0.1-3%; 5) PLOYSORBATE 20 is another oil in water emulsifier/solubilizer; 6) CETERETH 20 is useful in preparing oil-in-water emulsions, where it provides good stability, especially in combination with a second emulsifier such as glyceryl stearate.

Emulsifying wax may be obtained from many suppliers. For example, Lotioncrafter (Eastsound, Wash.) offers many emulsifying waxes, including emulsifying wax NF which is available as white pastilles having an HLB value of 14.9, and a recommended use rate of 2-25%, usually 3-5% for lotions and 5-10% for creams. They also offer mixtures of cetearyl alcohol (and) polysorbate 60 or emulsifying wax NF. See also PCT publication no. WO14134732.

In lieu of, or in addition to, an emulsifying wax, the compositions of the present invention may contain a surfactant. Suitable surfactants include anionic, cationic, amphoteric, zwitterionic and non-ionic, including those listed in U.S. Pat. No. 6,197,319. The surfactant functions to stabilize an emulsion between oil and water phases. Exemplary surfactants include, without limitation, saccharide and polysaccharide esters and ethers, such as sucrose stearate, sucrose cocoate and sorbitan stearate; oxyethylenated and/or oxypropylenated ethers of polyols such as glycerol; fatty acid esters of polyethylene glycol such as PEG-50 stearate; phosphoric esters such as oleth-10 phosphate and salts thereof, such as diethanolamine salts; oxyethylenated and/or oxypropylenated ethers of fatty alcohols such as ceteareth-30; alkyl ether sulphates such as sodium lauryl ether sulphate; isethionates; betaine derivatives; and mixtures thereof.

Further examples of nonionic surfactants include polyoxyethylene lauryl ethers; polyoxyethylene alkylphenol ethers; polyoxyethylene alkyl esters; polyoxyethylene sorbitan alkyl esters; polyethylene glycol (PEG); polypropylene glycol; diethylene glycol; ethoxylated trimethylnonanols; silicone alkanolamides; polyoxyethylene alkyl ethers; silicone esters; silicone glycosides; other fatty acid esters of polyols such as sorbitol and glyceryl mono-, di-, or tri-oleates or stearates; glyceryl or polyethylene glycol laurates; polyoxyethylene sorbitan monoleates; fatty acid esters of polyethylene glycol such as PEG monostearate and PEG monolaurate); polyoxyalkylene-substituted silicones (rake or ABn types); and polyoxyethylenated fatty acid esters, e.g., polyoxyethylenated stearate or oleate esters of sorbitol.

Additional exemplary anionic surfactants include amino acid derivatives such as N-acylglutamates, N-acylglycinates and acylsarcosinates; taurates and N-acyl N-methyltaurates; carboxylates such as sodium 2-(2-hydroxyalkyloxy)acetate; alkyl sulfates, alkyl ether sulfates and oxyethylenated derivatives thereof; isethionates and N-acylisethionates; sulfosuccinates; alkylsulfoacetates; and fatty acid soaps, and mixtures thereof.

Additional examples of amphoteric and zwitterionic surfactants include betaines and N-alkylamidobetaines; sultaines; alkyl polyaminocarboxylates; and alkylamphoacetates. The compositions of the present disclosure may include any one or more of these anionic, cationic and amphoteric surfactants.

The compositions of the present disclosure may contain an oil. The oil may be a synthetic oil or a natural oil such as coconut oil. Coconut oil is advantageously included in personal care compositions because it reportedly has moisturizing, skin softening, anti-aging, and anti-microbial properties. The coconut oil may be virgin grade and/or cold pressed. Another suitable oil is hemp seed oil, optionally cold pressed and/or unrefined. Hemp seed oil reportedly has the benefits of being a natural SPF 6, functions as an aid to Vitamin D absorption, reduces skin pore size, and has a high concentration of Omega 6 and Omega 3 which help rebuild epidermal lipids. Another suitable oil is argan oil from the argan tree. Argan oil reportedly has the benefits of being a natural SPF 30, has a light consistency similar to human sebum, contains vitamin E and essential fatty acids, reduces inflammation, minimizes the appearance of wrinkles and blemishes, heals scars due to containing triterpenoids, has disinfectant and anti-fungal properties making it helpful for cleansing, and a pleasant odor. Another suitable oil is shea butter. Shea butter reportedly has a natural SPF rating of 6, contains Vitamin E, has anti-inflammatory properties, may treat eczema, psoriasis, bites, cuts, cracks, burns, etc., has moisturizing properties as well as skin strengthening and regenerating properties, and stimulates collagen production. Another suitable oil is sunflower seed oil. Sunflower seed oil reportedly has a light consistency, similar to human sebum, contains vitamins E, A, and D as well as essential fatty acids and carotenoids. Another suitable oil is neem oil (azadirachta indica). Neem oil reportedly has a Natural SPF 15 rating, as well as having antiseptic, antiviral, anti-bacterial, anti-fungal, and insecticidal properties. Another suitable oil is jojoba oil, which is technically a liquid wax ester. Jojoba oil is reportedly a natural SPF 4+, has medium consistency very similar to human sebum, and has both anti-bacterial and anti-inflammatory properties. Yet another suitable oil is sweet almond oil. Sweet almond oil reportedly has a natural SPF 5, a light to medium consistency somewhat similar to human sebum, and contains calcium, potassium, magnesium, as well as Vitamins E, A, B1, B2, and B6.

The oil may be a so-called essential oil, which refers to a natural oil typically obtained by distillation and having the characteristic fragrance of the plant or other source from which it is extracted, sometimes used for aromatherapy. Examples of essential oils include Allspice essential oil (botanical name: *Pimenta officinalis*), Aniseed (Anise) essential oil (botanical name: *Pimpinella anisum*), Basil essential oil (botanical name: *Ocimum basilicum*), Basil essential oil (botanical name: *Ocimum basilicum*), Bergamot essential oil (botanical name: *Citrus bergamia*), Black Pepper (*Piper nigrum*) essential oil (botanical name: *Piper nigrum*), Blue Tansy (*Tanacetum annuum*) essential oil (botanical name: *Tanacetum annuum*), Cajeput essential oil (botanical name: *Melaleuca cajuputi*), Cajeput essential oil (botanical name: *Melaleuca cajuputi*), Camphor essential oil (botanical name: *Cinnamomum camphora*), Carrot Seed essential oil (botanical name: *Daucus carota*), Catnip essential oil (botanical name: *Nepeta cataria*), Cedarwood Atlantica essential oil (botanical name: *Cedrus atlantica*), Cedarwood Himalayan essential oil (botanical name: *Cedrus deodora*), Cedarwood Virginian essential oil (botanical name: *Juniperus virginiana*), Chamomile German (Blue) essential oil (botanical name: *Matricaria chamomilla*), Chamomile Roman essential oil (botanical name: *Chamaemelum nobile*), Cinnamon Bark essential oil (botanical name: *Cinnamomum verum*), Cinnamon Cassia essential oil (botanical name: *Cinnamomum cassia*), Cinnamon Leaf essential oil (botanical name: *Cinnamomum verum*), Citronella essential oil (botanical name: *Cymbopogon winterianus*), Clary Sage essential oil (botanical name: *Salvia sclarea*), Clove Bud essential oil (botanical name: *Syzygium aromaticum*), Coffee essential oil (botanical name: *Coffea Arabica*), Copaiba Balsam essential oil (botanical name: *Copaifera officinalis*), Coriander essential oil (Botanical name: *Coriandrum sativum*), Cypress essential oil (botanical name: *Cupressus sempervirens*), Dill Weed essential oil (botanical name: *Anethum graveolens*), Eucalyptus (Lemon) essential oil (botanical name: *Eucalyptus citriodora*), Eucalyptus globulus essential oil (botanical name: *Eucalyptus globulus*), Eucalyptus radiata essential oil (botanical name: *Eucalyptus radiate*), Fennel (Sweet) essential oil (botanical name: *Foeniculum vulgare* dulce), Fir Needle essential oil (botanical name: *Abies sibirica*), Frankincense carteri essential oil (botanical name: *Boswellia carteri* or *Boswellia sacra*), Frankincense frereana essential oil (Botanical name: *Boswellia frereana*), Frankincense serrata essential oil (Botanical name: *Boswellia serrata*), Garlic essential oil (botanical name: *Allium sativum*), Geranium Bourbon essential oil (botanical name: *Pelargonium×asperum*), Geranium Egyptian essential oil (botanical name: *Pelargonium×asperum*), Ginger Root Extract (botanical name: *Zingiber officinalis*), Grapefruit Pink essential oil (botanical name: *Citrus×paradise*), Helichrysum italicum essential oil (botanical name: *Helichrysum italicum*), Helichrysum splendidum essential oil (botanical name: *Helichrysum splendidum*), Jasmine Essential Oil (botanical name: *Jasminum grandiflorum*), Juniper Berry essential oil (botanical name: *Juniperus communis*), Laurel Leaf essential oil (botanical name: *Laurus nobilis*), Lavandin essential oil (botanical name: *Lavandula intermedia*), Lime essential oil (botanical name: *Citrus aurantifolia*), Mandarin essential oil (botanical name: *Citrus reticulate*), Marjoram essential oil (botanical name: *Origanum majorana*), May Chang essential oil (botanical name: *Litsea cubeba*), Myrrh essential oil (botanical name: *Commiphora myrrha*), Neroli essential oil (botanical name: *Citrus×aurantium*), Niaouli essential oil (botanical name: *Melaleuca quinquenervia*), Nutmeg essential oil (botanical name: *Myristica fragrans*), Orange (Blood) essential oil (botanical name: *Citrus sinensis*), Orange (Sweet) essential oil (botanical name: *Citrus sinensis*), Oregano (*Origanum*) essential oil (botanical name: *Origanum vulgare*), Palmarosa essential oil (botanical name: *Cymbopogon martini*), Patchouli (Dark) essential oil (botanical name: *Pogostemon cablin*), Pepper, Black essential oil (botanical name: *Piper nigrum*), Peppermint essential oil (botanical name: *Mentha× piperita*), Petitgrain essential oil (botanical name: *Citrus aurantium*), Pine essential oil (botanical name: *Pinus silvestris*), Ravensara essential oil (botanical name: *Ravensara aromatic*), Rosalina essential oil (botanical name: *Melaleuca ericifolia*), Rose (botanical name: *Rosa×damascene*), Rosemary essential oil (botanical name: *Rosmarinus officinalis*), Sage (Dalmatian) essential oil (botanical name: *Salvia officinalis*), Sandalwood (Australian) essential oil (botanical name: *Santalum spicatum*), Spearmint essential oil (botanical name: *Mentha spicata*), Spruce essential oil (botanical name: *Picea mariana*), Tangerine essential oil (botanical name: *Citrus reticulate*), Tansy (Blue) essential oil (botanical name: *Tanacetum annuum*), Tea Tree essential oil (botanical name: *Melaleuca alternifolia*), Thyme (Red) essential oil (botanical name: *Thymus vulgaris*), Turmeric essential oil (botanical name: *Curcuma longa*), Vanilla Oleoresin (botanical name: *Vanilla planifolia*), Vetiver essential oil (botanical name: *Vetiveria zizanoides*), and Wintergreen essential oil (botanical name: *Gaultheria procumbens*). These are exemplary oils that may be included in a formulation of the present disclosure.

The compositions of the present disclosure may contain a fatty acid. The fatty acid may have from about 10 to about 28 carbon atoms, i.e., be a C10-C28 fatty acid. For example, the fatty acid may be a saturated fatty acid having from about 10 to about 28 carbon atoms. The saturated fatty acid may be linear, where examples of linear saturated fatty acids include capric acid (decanoic acid), undecylic acid (undecanoic acid), lauric acid (dodecanoic acid), tridecyl acid (tridecanoic acid), myristic acid (tetradecanoic acid), pentadecylic acid (pentadecanoic acid), palmitic acid (hexadecanoic acid), margaric acid (heptadecanoic acid), stearic acid (octadecaonic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric (tetracosanoic acid), pentacosylic acid (pentacosanoic acid), cerotic acid (hexacosanoic acid), heptacosylic acid (heptacosanoic acid), and montanic acid (octacosanoic acid), where terms in parentheses are alternative names.

Alternatively, the fatty acid may be an unsaturated fatty acid. Examples of unsaturated fatty acids include, without limitation, α-linolenic acid, stearidonic acid, eicosapentaenoic acid, docosahexaenoic acid, linoleic acid, γ-linolenic acid, arachidonic acid, meat, docosatetraenoic acid, palmitoleic acid, vaccenic acid, paullinic acid, oleic acid, elaidic acid, gondoic acid, erucic acid, nervonic acid, and mead acid.

The compositions of the present disclosure may contain a moisturizing agent. Exemplary moisturizing agents include, without limitation, glycerin and other polyols such as sorbitol and trehalose, lower molecular weight aliphatic diols such as butylene glycol and propylene glycol, polyoxyethylene polymers such as polyethylene glycol (PEG) 200 and PEG400, hyaluronic acid and derivatives thereof, and urea.

In one embodiment the hyaluronic acid has a molecular weight of about 10,000 Daltons to about 1,100,000 Daltons. When the molecular weight of the hyaluronic acid is less than about 10 k Daltons, the viscosity-enhancing effect of the hyaluronic acid is below a desired amount for a creamy formulation, and when the molecular weight of the hyaluronic acid is greater than about 1.1 million Daltons, the color stability of the formulation is poor. A desired range of molecular weight for the hyaluronic acid component of a formulation of the present disclosure that includes silver particles is about 12,000 Daltons to about 1.1 million Daltons. In one embodiment, a formulation contains two different hyaluronic acid polymers, one having a molecular weight of about 12,000 Daltons and the other having a molecular weight of about 1,1000,000 Daltons. In one embodiment, molecular weight refers to weight average molecular weight.

In one embodiment the hyaluronic acid is present in a formulation of the present disclosure at a concentration of 0.1 wt % to 2.5 wt %, with the maximum concentration optionally being 2.2 wt %, or 2.1 wt %, or 2.0 wt %, or 1.9 wt %, or 1.8 wt %, or 1.7 wt %, or 1.6 wt %, or 1.5 wt %. When too much hyaluronic acid is present in a silver-containing formulation of the present disclose then discoloration of the formulation may be observed. When the concentration of hyaluronic acid is less than 0.1 wt %, or less than 0.2 wt %, or less than 0.25 wt %, or less than 3 wt %, then the moisturizing efficacy of the formulation is reduced, since hyaluronic acid is a good moisturizing agent.

The compositions of the present disclosure may contain an emollient. Emollients, as used herein, refer to materials used for the prevention or relief of dryness, as well as for the protection of the skin. Examples of emollients include, without limitation, stearyl alcohol, glycerol monoricinoleate, glycerol monostearate, mink oil, cetyl alcohol, isopropyl isostearate, stearic acid, isobutyl palmitate, isocetyl stearate, oleyl alcohol, isopropyl luarate, hexyl laurate, decyl oleate, octadecan-2-ol, isocetyl alcohol, eicosanylalcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernal oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitic acid, 5 isopropyl linoleate, lauryl lactate, myristyl lactate, decyl oleate, and myristyl myristate.

The compositions of the present disclosure may contain a pH adjusting agent, also sometimes referred to as a pH controlling agent, and also referred to as an acid or a base. Examples of such agents include acids, such as water soluble acids which may be an organic acid or an inorganic (mineral) acid. Examples include, without limitation, hydrochloric acid, sulphuric acid, phosphoric acid, monocarboxylic acid such as acetic acid and lactic acid, and polycarboxylic acids such as succinic acid, adipic acid, and citric acid. The pH adjusting agent may be a base, which may be an organic or inorganic base. Examples include water soluble organic bases such as ethanolamine, diethanolamine and triethanolamine, as well as the inorganic bases sodium hydroxide and potassium hydroxide, to name a few.

The compositions of the present disclosure may contain vitamin or vitamin derivative. For example, the vitamin or vitamin derivative may be lipid soluble, where examples include, without limitation, retinol (vitamin A), ergocalciferol (vitamin D2), cholecalciferol (vitamin 5 D3), phytonadione (vitamin K1), and tocopherol (vitamin E). As another example, the vitamin or vitamin derivative may be water-soluble, where examples include, without limitation, ascorbic acid (vitamin C), thiamin (vitamin B1) niacin (nicotinic acid), niacinamide (vitamin B3), riboflavin (vitamin B2), pantothenic acid (vitamin BS), biotin, folic acid, pyridoxine (vitamin B6), and cyanocobalamin (vitamin B12).

Other exemplary vitamins that may be included in the compositions of the present disclosure include, without limitation, tocopheryl nicotinate, tocophereth-18, tocopheryl linoleate (vitamin E linoleate), tocophereth-50 (ethoxylated vitamin E derivatives), retinyl acetate (vitamin A acetate), PPG-2 tocophereth-5, PPG-5 tocophereth-2, PPG-10 tocophereth-30, PPG-20 15 tocophereth-50, tocophereth-12, PPG-30 tocophereth-70, retinyl propionate (vitamin A propionate), PPG-70 tocophereth-100 (propoxylated and ethoxylated vitamin E derivatives), retinyl palmitate 10 (vitamin A palmitate), tocopheryl succinate (vitamin E succinate), sodium tocopheryl phosphate, ascorbyl palmitate, retinyl linoleate (vitamin A linoleate), ascorbyl glucoside, ascorbyl dipalmitate, tocophereth-5, tocophereth-10, ascorbyl tocopheryl maleate, ascorbyl tetraisopalmitate, tetrahexadecyl ascorbate, tocopheryl acetate (vitamin E acetate), potassium ascorbyl and tocopheryl phosphate. See, e.g., US2013331428 AA, for formulations that include retinoids. In one embodiment the vitamin, e.g., vitamin E, is present in the formulation at a concentration of at least about 0.5 wt % but less than about 1.0 wt %.

The compositions of the present disclosure may contain a sunscreen agent. Examples include, without limitation, aminobenzoic acid, cinoxate, diethanolamine 10 methoxycinnamate, digalloyl trioleate, dioxybenzone, ethyl 4-[bis(Hydroxypropyl)] aminobenzoate, ethyl hexyl methoxycinnamate, glyceryl aminobenzoate, homosalate, lawsone with dihydroxyacetone, menthyl anthranilate, octocrylene, octyl salicylate, phenylbenzimidazole sulfonic acid, red petrolatum, sulisobenzone, titanium dioxide, and trolamine salicylate.

The compositions of the present disclosure may contain a UV absorber. The UV absorber may be PABA or a PABA derivative such as allatoin PABA, butyl PABA, dimethyl PABA ethyl cetearyldimonium tosylate, ethyl dihydroxypropyl PABA, ethyl PABA, glyceryl PABA, octyl dimethyl PABA, propyl dihydroxypropyl PABA, PEG-25 pentyl dimethyl PABA, and triPABA panthenol. The UV absorber may be a cinnamate compound such as DEA-methoxycinnamate, diisopropyl ethyl cinnamate, diisopropyl methyl cinnamate, ethyl 25 diisopropylcinnamate, ethyl methoxycinnamate, glyceryl octanoate dimethoxycinnamate, isobutyl methoxycinnamate, isopropyl methoxycinnamate, isoamyl p-methoxycinnamate, ethyl hexyl 30 methoxycinnamate, and potassium methoxycinnamate. The UV absorber may be a salicylate compound such as benzyl salicylate, glycol salicylate, isopropylbenzyl salicylate, menthyl salicylate, octyl salicylate, propyl salicylate and TEA-salicylate. See, e.g., U.S. Pat. No. 8,486,463.

These sunscreen agents and/or UV absorbers may absorb ultraviolet light between about 290-320 nanometers (the UV-B region) and/or absorb ultraviolet light in the range of 320-400 nanometers (the UV-A region).

The compositions of the present disclosure may contain a skin protectant. Examples include, without limitation, allantoin, an aluminum salt such as aluminium acetate, aluminium hydroxide and aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, and a zinc salt such as zinc acetate, zinc carbonate and zinc oxide.

The compositions of the present disclosure may contain preservative and/or a biocide. Examples include, without limitation, paraben derivatives, hydantoin derivatives, chlorhexidine and its derivatives, imidazolidinyl urea, phenoxyethanol, salicylate derivatives, triclosan, ciclopirox olamine, hexamidine, oxyquinoline and its derivatives, PVP-iodine, and zinc salts and derivatives such as zinc pyrithione.

The compositions of the present disclosure may contain a therapeutic agent, in which case the composition may be used to deliver a therapeutic agent to a subject in need thereof. Exemplary therapeutic agents include, without limitation, acetominophen, amphetamines, anesthetics, aspirin, barbiturates, benzocaine, benzodiazepine, "caine" anesthetics, cancer-treating agents, catecholamines, cephalosporins, codeine, diclofenac, dipyridamole, epinephrine, hormones (see, e.g., PCT publication WO 2015/038951), indomethicane, lidocaine, macrolides, morphine, NSAIDs, opiods, penicillins, perbuterol, procaine, prostaglandins, scopolamine, steroids, sulphonamides, suramin, tetracyclines, thiopental, ticonazole, and theophylline. In one embodiment the composition comprises lidocaine in an anesthetically effective amount for a topical anesthetic.

The compositions of the present disclosure may be used to combat acne, i.e., to prevent, treat or control the occurrence of acne, in which case the compositions will contain one or more anti-acne therapeutic agents. Acne medications work by reducing oil production, speeding up skin cell turnover, fighting bacterial infection and/or reducing inflammation. In one embodiment the composition comprises a retinoid. Retenoid drug are derived from vitamin A and include tretinoin (such as in Avita and Retin-A), adapalene (such as in Differin) and tazarotene (such as in Tazorac and Avage). Creams and lotions containing such an ingredient generally work by preventing plugging of the hair follicles. In another embodiment the composition comprises an antibiotic. These work by killing excess skin bacteria and reducing redness. In another embodiment, the composition contains benzoyl peroxide. Benzoyl peroxide has antibacterial, peeling (keratolytic), and drying actions. For example, the composition may contain both an antibiotic and benzoyl peroxide, where the benzoyl peroxide reduces the likelihood of developing antibiotic resistance. Examples include clindamycin with benzoyl peroxide (such as in Benzaclin, Duac, Acanya) and erythromycin with benzoyl peroxide (such as in Benzamycin). In another embodiment, the composition contains salicylic acid. Topical administration of salicyclic acid creates a mild chemical peel, whereby the skin cells in the top layers of the skin are removed. The compositions of the present disclosure may contain an exfoliating agent which removes dead skin cells from the epidermis, the top layer of the skin, where suitable exfoliating agents include salicyclic acid as mentioned previously, and also include other effective exfoliating agents such as glycolic acid and lactic acid.

The present disclosure provides an acne treatment or combatting composition comprising silver particles and one or more of water, alcohol such as propylene glycol or polyethylene glycol, and an exfoliant such as salicylic acid or glycolic acid. In preparing an acne-combatting formulation of the present invention, the formulation contains silver particles, such as silver particles with Ag +2 as mentioned elsewhere herein. In one embodiment, the silver is present at a concentration of at least about 1 ppm, or 5 ppm, or 8 ppm, or 10 ppm, or 12 ppm, or 15 ppm, and at a concentration of less than about 50 ppm, or 45 ppm, or 40 ppm, or 35 ppm, or 32 ppm, or 30 ppm, or 25 ppm. For example, the formulation may contain between 10 and 32 ppm of silver particles. As the concentration of silver is decreased, the antimicrobial effectiveness of the silver undesirably decreases, and as the concentration of the silver is increased, the light sensitivity of the formulation undesirably increases, which leads to discoloration of the formulation to, e.g., a gray color. The acne-combatting formulation may also contain salicylic acid at a concentration of about 0.5% to about 2.0%, e.g., from about 0.2%, or from about 0.3%, or from about 0.4%, or from about 0.5%, or from about 0.6%, to about 3.0%, or to about 2.5%, or to about 2.0%, or to about 1.5%. As used herein and through the specification, % values refer to weight percent of the total weight of the formulation. As the concentration of salicylic acid is decreased, the exfoliating properties of salicylic acid undesirably diminishes, while if the concentration of salicylic acid is increased, the salicylic acid does not remain suspended or solubilized in the formulation. An acne-combatting formulation may also contain propylene glycol at a concentration of from about 7% to about 10%, e.g., from about 5%, or from about 6%, or from about 7%, or from about 8% to about 9%, or to about 10%, or to about 11%, or to about 12%. As the concentration of propylene glycol decreases, the ability of the salicylic acid to remain dissolved or suspended in the formulation diminishes, while as the concentration of propylene glycol increases, the rheology of the formulation is undesirably reduced. An acne-combatting formulation may also contain a polyacrylic acid, e.g., Carbomer® (Lubrizol Corp.) having a desired level of cross-linker, distance between cross-links, uniformity of cross-linking, degree of branching and the particle size, e.g., Carbomer Ultrez 30® which is a crosslinked polyacrylic acid. The Carbomer® may be present in the formulation at a concentration of from about 0.5% to about 1.5%, e.g., from about 0.3%, or from about 0.4%, or from about 0.5%, or from about 0.6% and to about 2.0%, or to about 1.7%, or to about 1.5%, or to about 1.3%. As the concentration of Carbomer® increases, the rheology (viscosity) of the formulation increases, and as the concentration of Carbomer® decreases, the rheology (viscosity) of the formulation decreases, so that a concentration of from about 0.5% to about 1.5% provides a desirable viscosity. An acne-combatting formulation may also contain triethanol at a concentration of about 1.5% to about 3%, for example, from about 1.0%, or from about 1.2%, or from about 1.5%, or from about 1.7% to about 4%, or to about 3.5%, or to about 3%, or to about 2.5%. As the amount of triethanolamine in the formulation decreases, the pH of the formulation becomes undesirably low and also the viscosity of the formulation is undesirably reduced. Conversely, as the amount of the triethanolamine in the formulation increase, the pH of the formulation becomes undesirably high and also the viscosity of the formulation is undesirably increased, so that a concentration from about 1.5% to 3% provides a desired pH and viscosity for the formulation. An acne-combatting formulation of the present disclosure may contain more than one, or all, of these listed components, e.g., silver particles (including silver in the +2 oxidation state) at a concentration of 10-32 ppm, salicylic acid at a concentration of 0.5-2 wt %, propylene glycol at a concentration of 7-10 wt %, Carbomer, e.g., Carbomer Ultrez 30 at a concentration of 0.5-1.5 wt %, and triethanolamine at a concentration of 1.5-3 wt %.

The compositions of the present disclosure may contain a lubricious agent or lubricant. When a composition of the present disclosure contains a lubricious agent and that composition is applied topically, the composition will impart lubricity to the tissue to which it is applied. For example, the composition may contain glycerin, which may function as a lubricious agent. As another example, the composition may contain a cellulose derivative, such as hydroxyethylcellulose (HEC) and carboxymethyl cellulose. The lubricious composition of the present disclosure may contain a lubricious agent so as to create a personal lubricant, where the personal lubricant may contain other components. See, for example, U.S. Pat. No. 6,114,398 (a composition for preventing and treating itching on a body part by reducing any of *Candida* species, *Neisseria gonorrhoeae* species, *Peptostreptococcus lacrimalis* species, *Gardnerella vaginalis* species present, the composition comprising glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4); U.S. Pat. No. 4,981,686 (a personal lubricant composition, particularly a vaginal lubricant, having one or more of good lubricating ability, pleasant fragrance and taste, greaselessness, nonstaining, water solubility, nonirritating, humectant and harmless if ingested; soothes vaginal tissue, does not prevent pregnancy and does not impede sperm motility); 2013/0251818 (a personal lubricant containing royal jelly (see, e.g., U.S. Pat. No. 5,871,754), a glow powder and xylitol), 2013/184233 (a skin lubrication lotion that functions as a skin rubbing anti-friction barrier compound to prevent skin rashes from burning of skin from excessive rubbing, the lotion including one or more of a lubricant; a skin numbing ingredient such as lidocane; a vitamin ingredient, an ingredient that causes human skin to tingle, sodium benzoate, potassium sorbate, citric acid, propylene glycol, xanthan gum, and guar gum), and 2009/0185995 as well as PCT publication nos. WO 2014/055627 (a personal lubricant composition that includes at least one silicone-containing component, and a hydrophilic component comprising water and a polyol which provide advantages such as to tactile and sensory feel); WO 2014/055621 (a non-irritating personal lubricant composition comprising a silicone fluid carrier and at least one sensorial agent, the composition having a viscosity of at least 175 centistokes); and WO 2009/016350 (a personal lubricant composition comprising a vasodilator and at least one coolant, such as menthol or a cyclic carboxamide such (−) isopulegol).

As mentioned above, the present disclosure provides a personal lubricant comprising silver particles, water and a thickening agent such as hydroxyethylcellulose (HEC). In preparing a personal lubricant, the formulation contains silver particles, such as silver particles with Ag +2 as mentioned elsewhere herein. In one embodiment, the silver is present at a concentration of at least about 1 ppm, or 5 ppm, or 8 ppm, or 10 ppm, or 12 ppm, or 15 ppm, and at a concentration of less than about 50 ppm, or 45 ppm, or 40 ppm, or 35 ppm, or 32 ppm, or 30 ppm, or 25 ppm. For example, the formulation may contain between 10 ppm and 32 ppm of silver particles. As the concentration of silver is decreased, the antimicrobial effectiveness of the silver undesirably decreases, and as the concentration of the silver is increased, the light sensitivity of the formulation undesirably increases, which leads to discoloration of the formulation to, e.g., a gray color. A personal lubricant formulation may also contain propylene glycol at a concentration of from about 2% to about 5%, e.g., from about 1%, or from about 2%, or from about 3%, to about 4%, or to about 5%, or to about 6%, or to about 7%. As the concentration of propylene glycol decreases, the lubricity of the formulation undesirably decreases, and as the concentration of propylene glycol increases, the viscosity of the formulation undesirably decreases, so that a concentration of about 2-5 wt % is a suitable concentration. A personal lubricant formulation of the present invention may contain hydroxyethylcellulose (HEC) and/or hydroxypropyl methylcellulose (HPMC) as a thickening agent, at a concentration of about 1.25 wt % to about 2.5 wt %, e.g., from about 0.75 wt %, or from about 1.0 wt %, or from about 1.25 wt %, or from about 1.5 wt % to about 2 wt %, or to about 2.25 wt %, or to about 2.5 wt %, or to about 2.75 wt %, or to about 3 wt %. As the concentration of thickening agent increases, the viscosity of the personal lubricant increases, and as the concentration of thickening agent decreases, the viscosity of the personal lubricant decreases, so that a concentration of about 1.25-2.5 wt % is suitable. The personal lubricant may contain each of silver (e.g., in the +2 oxidation state) particles at a concentration of about 10-32 ppm, thickening agent such as HEC or HPMC at a concentration of 1.25-2.5 wt %, and propylene glycol at a concentration of about 2-5 wt %.

The compositions of the present disclosure may contain a natural plant extract, that is, an extract from flower, tree, root, or the like. In one embodiment the extract is from aloe. Topical aloe has been reported to inhibit infection and promote healing of minor burns and wounds, frostbite, as well as in skin affected by diseases such as psoriasis and seborrheic dermatitis. Other exemplary include ginger flower (see, e.g., CN patent 103494737); sugar apple and rosemary extracts, optionally in combination with prickly ash extract (see, e.g., WO 2015/066352); an extract of tapirira guianensis (see, e.g., WO15036704); a polygonum bistorta extract (see, e.g., WO14155012 A1); an extract from a seed of the *Nicotiana* species (see, e.g., US2014356295); a silver ear extract (see, e.g., WO14191056 A1); an extract of water hyacinth (see, e.g., EP2777709); an extract of zooplankton (see, e.g., WO14016086), an extract containing chicoric acid (see, e.g., EP2848286); or an extract that contains riboflavin and/or salts or hydrates thereof (see, e.g., WO15033316), to name a few.

The compositions of the present disclosure may contain one or more amino acids. In one embodiment the amino acid is L-arginine, which is reported to have anti-aging effects. See, e.g., Mohamed Z. Gad, Journal of Advanced Research, Volume 1, Issue 3, July 2010, Pages 169-177. In one embodiment the amino acid is L-carnitine. In one embodiment the amino acid is L-lysine. Other suitable amino acids include alanine, asparagine, aspartic acid, cysteine, cystine, glutamic acid, glutamine, glycine, histidine, isoleucine, leucine, methionine, phenylalanine, proline, serine, threonine, tryptophan, tyrosine and valine. When present, the amino acid, e.g., arginine, may be present in a concentration of at least about 0.05 wt %, e.g., 0.06 wt %, or 0.7 wt %, or 0.8 wt %, or 0.9 wt %, or 1.0 wt %, in order to provide the desired efficacy, e.g., the pH may be too low if too little amino acid is used. However, too much amino acid should be avoided, since silver can oxidize amino acids and cause the release of ammonia, which leads to an undesirable rancid oil phase. In the formulations of the present disclosure, the amino acid concentration may be less than 0.5 wt %, or less than 0.4 wt %, or less than 0.3 wt %, or less than 0.2 wt %, or less than 0.1 wt % of the weight of the formulation. In one embodiment the amino acid, e.g., L-arginine, is present in the formulation at a concentration of between 0.08 wt % and 0.1 wt %.

The composition of the present disclosure may contain a dietary supplement that imparts health benefits. For example, the composition may contain equol, also known as 4',7-isoflavandiol. Other suitable supplements include alpha lipoic acid, black cohosh, calcium, chromium, coenzyme Q10, DHEA, flaxseed, folic acid, ginko, glucosamine, melatonin, niacin, magnesium, probiotics, extract from red yeast rice, St. John's wort, vitamin c, vitamin D, vitamin E, SAM-e, saw palmetto, selenium, turmeric, valerian, whey protein, and yohimbe.

The composition of the present disclosure may contain a fragrance or an odor mask. Examples of fragrances and odor masks, include, without limitation, menthol, anethole, carvone, eugenol, limonene, ocimene, n-20 decylalcohol, citronellol, α-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, perilla oil, wintergreen oil, clove oil, and *eucalyptus* oil.

In addition, the formulations, preparations, compositions and the like as disclosed and/or claimed in the following patent documents may incorporate colloidal silver particles as disclosed herein, to provide compositions of the present invention: WO14136993, WO15098433, WO15052804, WO15045167, WO14199936, WO14196602, WO14174868, WO14136886, WO14129240, WO13132878, WO14084099, WO14077334, WO14077189, WO14069173, WO14069400, WO14069403, WO14069388, WO14058048, WO14058060, WO14050487, US2015202137, US2014004210, WO13146891, WO13146797, WO13147012, WO13136890, WO13136616, WO13128736, US2014343169, WO13118836, US2014357721, WO13115099, US2014356401, US2014348765, WO13099378, US2014343170, US2015005396, US2014323591, WO13077072, US2015157546, US2014255323, WO13061712, US2014235732, US2014255527, WO13047204, WO13047196, WO13038861, WO13031327, US2013344013, US2014205552, US2014186281, US2014219939, US2014134255, WO12172622, US2014105840, US2014086864, WO12161215, WO12157694, WO12157587, US2014066358, WO12141255, WO12133825, WO12132603, US2014017191, US2014018444, WO12133293, US2014024724, WO12132951, WO12124436, WO12124766, US2014010901, WO12121309, US2013331468, WO12118055, WO12115247, US2013336908, WO12101741, WO12098765, WO12090297, WO12090581, WO12086579, WO12081446, WO12077639, WO12073928, WO12070309, US2013189335, WO12056959, US2013231401, US2014148516, WO12046500, WO12043614, US2013142853, WO12035904, US2013121939, and WO12017733. Each of these patent documents is incorporated herein by reference.

The foregoing are exemplary of the components that may be present in an emulsion of the present invention. Particularly when the emulsion is part of a cosmetic, dermatalogic or pharmaceutical composition, the composition may be contain additional ingredients that make the composition particularly well-suited for the intended use. For instance, one or more of antioxidants, anti-inflammatory agents, anti-acne agents, antimicrobial agents, collagen, chitosan, astringents, humectants, moisturizers, pH adjusters, skin bleaching/lightening agents, skin soothing/healing agents and agents that help decrease the appearance of signs of aging may be incorporated into the emulsion of the present disclosure. Also, lightening agents, darkening agents such as self-tanning agents, shine control agents, anti-mycotic agents, anti-parasite agents, external analgesics, sunscreens, photoprotectors, depigmenting agents, keratolytic agents, detergents/surfactants, nutrients, vitamins, energy enhancers, anti-perspiration agents, deodorants, hair removers, firming agents, anti-callous agents, and agents for hair, nail, and/or skin conditioning may be included in the compositions of the present disclosure. The composition may contain a pigment (see, e.g., US2013266621).

The International Cosmetic Ingredient Dictionary and Handbook (15th Edition, 2014), published by the Cosmetic, Toiletries & Fragrance Association, describes a wide variety of non-limiting cosmetic and dermatopharmaceutical ingredients commonly used in the skin care industry, which are suitable for use in preparing emulsions having colloid silver particles as described herein. The disclosure of The International Cosmetic Ingredient Dictionary and Handbook (15th Edition, 2014), is incorporated by reference herein in its entireties for its teachings of cosmetic and dermatopharmaceutical ingredients.

As stated above, the present invention provides emulsions which incorporate colloidal silver, preferably in particulate form, and which are particularly useful as cosmetic, dermatologic or therapeutic formulations, particularly in the form of creams, serums, lotions, ointments, and the like. However, in another aspect, the compositions of the present disclosure are not in emulsion form, and in fact may be oil-free, i.e., they do not contain any oil component. In such compositions, the silver is typically utilized as an aqueous composition, e.g., the silver particles are dispersed and suspended in water, and such a composition can be used to provide the aqueous component of formulation In addition to the colloidal silver, which has been discussed above, the oil-free compositions may be prepared from the above-listed ingredients, where the identified ingredients may not be the exclusive ingredients that may be present in the formulation, but rather are options that may be employed in order to prepare the desired serum, lotion, cream, ointment etc. that is oil-free.

For example, in one embodiment, the present disclosure provides an oil-free composition comprising colloidal silver particles that is useful as a personal lubricant. In addition to water and colloidal silver particles, the personal lubricant of the present disclosure will contain a thickening agent such as hydroxyl ethyl cellulose (HEC). The thickening agent is present in such an amount as to impart the desired viscosity to the product. In one embodiment, the personal lubricant contains 2% by weight of thickening agent such as HEC, however greater or less amounts of thickening agent may be incorporated into the product as needed to achieve the desired viscosity of the product. Other ingredients such as those identified above, may also be added to the personal lubricant.

As another example, in one embodiment the present disclosure provides an oil-free composition comprising colloidal silver particles that is useful as an acne treatment medicament. In addition to colloidal silver particles and water, the acne treatment composition of the present disclosure comprises an exfoliant. Exemplary exfoliants include salicylic acid and glycolic acid. The acne treatment medicament may further comprise optional ingredients such as an alcohol. Exemplary alcohols include ethanol, propylene glycol and polyethylene glycol.

As another example, a formulation of the present disclosure may be formed from Silver Solution 20 ppm, and one or more of Caprylic/Capric Triglyceride, Octyldodecyl Myristate, Butylene Glycol, Tricaprylin, Ethylhexyl Stearate, Methyl Trimethicone, Peg-100 Stearate, Glycerin, *Butyrospermum parkii* (Shea Butter), Glyceryl Stearate, Cetearyl Alcohol, Polysorbate 60, *Prunus armeniaca* (Apricot) Kernel Oil, *Ribes nigrum* (Black Currant) Seed Oil, *Citrus aurantium dulcis* (Orange) Peel Oil, *Rosa Damascena* Flower Oil, *Cinnamomum camphora* (Camphor) Bark Oil, Linalool, Limonene, *Camellia cinensis* (White Tea) Leaf Extract, Sodium Pca, Dimethicone, Sodium Hyaluronate, Sorbitol, Ethylhexylglycerin, Caprylyl Glycol, Hexylene Glycol, Carbomer, Sodium Dehydroacetate, Potassium Hydroxide, and Phenoxyethanol.

As another example, a formulation of the present disclosure may formed from Silver Solution 20 ppm, and one or more of *Butyrospermum Parkii* (Shea) Butter, Glycerin, Caprylic/Capric Triglyceride, *Vitis vinifera* (Grape) Seed Oil, Dicaprylyl Carbonate, Dimethicone, *Prunus armeniaca* (Apricot) Kernel Oil, Cetearyl Alcohol, Glyceryl Stearate, *Cocos nucifera* (Coconut) Oil, *Prunus amygdalus dulcis* (Sweet Almond) Fruit Extract, Mel Extract/Honey Extract, Hydroxyethyl Acrylate/Sodium Acryloyldimethyl Taurate Copolymer, Tocopherol, Ethylhexylglycerin, Parfum/Fragrance, Xanthan Gum, Propylene Glycol, Sorbitan Isostearate, Polysorbate 60, Chlorphenesin, Peg-100 Stearate, Phenoxyethanol, Ceteareth-33, Benzyl Alcohol, Benzyl Benzoate, Hydroxyisohexyl 3-Cyclohexene Carboxaldehyde, Linalool, Citronellol, Butylphenyl Methylpropional, Coumarin, Hexyl Cinnamal, Limonene, and Geraniol.

The active components and ingredients as disclosed herein may be incorporated into a serum, lotion, cream or ointment of the present disclosure in an amount, or in amounts, that such components and ingredients provide efficacy, as will be known to one of ordinary skill in the art.

Serums, Lotions, Creams and Ointments

The present disclosure provides colloidal silver particles in an emulsion, where the emulsion may be formulated as, for example, a health care product, beauty product or a pharmaceutical. The formulation may take the form of a serum, a lotion, a cream or an ointment, as four examples. The formulation is typically intended for topical administration.

In general, body cream is heavier and contains a higher viscosity, or sticky mixture of water and oil compared to a lotion. Creams penetrate the skin and provide a barrier that prevents more moisture loss from the skin than lotion. Creams, however, tend to feel greasier. A pharmaceutical or dermatology cream is usually an even mixture of 50 percent oil and 50 percent water. Creams are sometimes described as a semi-solid emulsion, half oil and half water. However, the ratio of water and oil in cosmetic cream and lotion varies and is also affected by other ingredients, such as paraffin. Because body cream is thicker, it is usually sold in a tub or jar container. Creams are typically easy to use and are preferred by many people. They spread easily, absorb quickly and wash off with water. Overall, they have a medium viscosity or heaviness, and are reasonably hydrating without feeling too heavy on your skin. Creams are always packaged in a tub or a tube; they are too thick to be dispensed in a pump. Creams are often used to treat acne in patients whose skin is somewhat dry, as the creams promote hydration. Creams are also more beneficial in lighter skin, which in general is more easily irritated than darker skin.

Body lotions are not as sticky and are more readily absorbed by the skin because they have a lower viscosity than body creams. This form of moisturizer usually has a higher water content, comes in a bottle and can be poured out in a liquid form. Lotion is good for skin that is not excessively dry or when it is preferable not to have a sticky, greasy feeling on the skin. Lotions are thinner than creams, and are often packaged in a pump. They absorb very quickly and feel very light on the skin. They are easier to distribute on hairy areas. Most over-the-counter body moisturizers are lotions.

Ointments are more viscous that lotions or creams. They often contain about 80% oil and 20% water. These products feel greasy, they do not absorb well into skin, and are generally not easy to use on large areas. They are 'occlusive,' which means they trap moisture and heat in very well. Ointments promote medication absorption over all other formulations. If an ingredient is in an ointment, it is always more potent than the exact same ingredient packaged in a cream or lotion. For example, amcinonide is a topical steroid. In an ointment it is considered high potency, and in a cream or lotion it is considered medium-high potency.

The formulation may be a serum. Serums are the newer cousin of creams and lotions and are currently very much in vogue in the cosmetics industry. Serums tend to be thick liquids and are usually (but not always) clear. They may be water based which makes them lightweight and quickly absorbed into the skin. Serums are light, fast-absorbing liquids used as an alternative or in addition to creams or lotions. The biggest difference between a serum and a cream or lotion is what the formulation doesn't include. Serums leave out occlusive, or airtight, moisturizing ingredients such as petrolatum or mineral oil that keep water from evaporating. They also contain fewer lubricating and thickening agents, like nut or seed oils. A serum often has a high concentration of active ingredients, including anti-aging ingredients such as antioxidants, peptides and skin brighteners such as kojic acid.

Many companies formulate serums for the delivery of topical active ingredients such as Vitamin C, equol, isoflavandiol, peptides, alpha hydroxy acids or retinols. For example, an exemplary serum of the present disclosure contains a high concentration alpha hydroxy formulation for hyperpigmentation and scars. Another serum of the present disclosure contains vitamin K and retinol to help to reduce the appearance of dark circles and fine lines. Another serum of the present disclosure contains 5% Vitamin C to help boost collagen production and even skin tone. Another serum of the present disclosure contains vitamin C and madecassoside to boost collagen production and even skin tone. Yet another serum of the present disclosure contains 5% matrixyl (a peptide) which boosts collagen production in order to reduce the appearance of wrinkles. Serums provide a concentrated way to get anti-aging ingredients into the skin and can be layered under other products without interfering with them. Because serums tend to be light and water based, most skin types can use them. Thus, the present disclosure provides anti-aging serums which are serums that include both anti-aging components and colloidal silver as disclosed herein.

Accordingly, in one embodiment the present disclosure includes colloidal silver incorporated into a serum, or in other words, a serum comprising colloidal silver as disclosed herein. The serum may or may not include an oil phase. If it does not contain an oil phase, then the formulation will not be an oil-in-water or water-in-oil emulsion as disclosed herein. Accordingly, in one embodiment, the present disclosure provides a serum that does not contain an emulsion, but does not colloidal silver. In another embodiment, the present disclosure provides a serum that does contain an emulsion and also contains colloidal silver. Thus, the serum may contain an oil-in-water emulsion, optionally a dilute oil-in-water emulsion which contains primarily water on a weight basis.

In summary, both creams and lotions are emulsions having a water and oil phase. The salient difference is the thickness. Lotions are a low-viscosity emulsion. Most lotions are oil in water emulsions but water in oil lotions also are formulated. Lotions are designed to be applied without heavy rubbing. Since they have a low viscosity, they usually are easily rubbed onto the skin. On the other hand, creams are much higher viscosity materials. They generally are semi-solid emulsions. Like lotions, creams can be either oil-in-water or water-in-oil emulsions. Oil-in-water creams are more comfortable and cosmetically acceptable as they are less greasy and more easily washed off using water. Water-in-oil creams are more difficult to handle but are more moisturizing as they provide an oily barrier that reduces water loss from the skin. Serums may or may not contain an emulsion, but typically contain primarily water as the carrier, and lesser amounts of oils than are typically found in a lotion, cream or ointment.

In one embodiment, the emulsions of the present invention are not incorporated into a gel. Gels typically have an alcohol base, and in one embodiment the formulations of the present disclosure do not include an alcohol base. In various embodiments, the formulations of the present disclosure do not include any alcohols having less than 8 carbon atoms, or less than 7 carbon atoms, or less than 6 carbon atoms, or less than 5 carbon atoms, or less than 4 carbon atoms, or less than 3 carbon atoms. In other embodiments, the formulations of the present disclosure may include alcohol, but only at low concentrations, e.g., less than 10%, or less than 8%, or less than 6%, or less than 5%, or less than 4%, or less than 3%, or less than 2%, or less than 1% of the overall weight of the formulation, where alcohols have less than 8 carbon atoms, or less than 7 carbon atoms, or less than 6 carbon atoms, or less than 5 carbon atoms, or less than 4 carbon atoms, or less than 3 carbon atoms. In each of the compositions and formulations described herein, in one embodiment the composition and formulation is free of volatile alcohol, which refers to alcohols have 1 or 2 or 3 or 4 or 5 carbon atoms. In each of the compositions and formulations described herein, in one embodiment the composition and formulation is alcohol free. In each of the compositions and formulations described herein, in one embodiment the composition and formulation is substantially alcohol free, which refers to a composition or formulation that contains less than 5 wt % of an alcohol having less than 6 carbons atoms.

Manufacturing Process

In one embodiment, the present disclosure provides methods of making an emulsion that contains colloidal silver. For example, the emulsion may be made from an oil phase and a water phase, where the water phase contains colloidal silver. At elevated temperature and with vigorous stirring, the oil phase may be gradually added to the water phase, or the water phase may be gradually added to the oil phase. An emulsifying wax or like agent should be present in order to stabilize the emulsion droplets. In various embodiments, the temperature at which the emulsion is prepared is within the range of 40° C. to 65° C., or within the range of 45° C. to 60° C., or within the range of 49° C. to 57° C., or within the range of 50° C. to 55° C. When the temperature is too low, one or more components of the formulation may precipitate from the formulation and/or the emulsion particle size is poor, while when the temperature is too high, the formulation may undergo an undesirable change in color. The emulsion formulations of the present disclosure may be prepared by combining oil and water phases at a temperature of less than 70° C., or less than 65° C., or less than 60° C., in order to avoid unwanted discoloration.

Depending on the exact formulation, the product may have the form of a lotion, cream, ointment, etc. As mentioned previously, a lotion is generally less viscous (less thick) than a cream, and a cream is generally less viscous (less thick) than an ointment. In one embodiment, the formulation of the present disclosure is a lotion. In another embodiment, the formulation of the present disclosure is a cream. In another embodiment, the formulation of the present invention is an ointment. In another embodiment, the formulation of the present invention is a serum. In another embodiment, the formulation of the present disclosure is not a gel.

For example, to prepare a lotion, about 75-85 parts, or about 80 parts (parts refer to grams for every 100 grams of final formulation) of ABL solution (an aqueous dispersion of silver particles from ABL Manufacturing LLC) is combined with about 5-10 parts, or about 6-8 parts, or about 7 parts of emulsifying wax, and about 5-10 parts or about 6-8 parts or about 7 parts of an oil such as coconut oil, and about 3-7 parts, or about 4-6 parts, or about 5 parts of fatty acid such as stearic acid, and about 0.1-1 parts, or about 0.3-0.8 parts, or about 0.5 parts of a vitamin such as vitamin E, and a pH controlling agent as needed, for example, about 0.1-0.5 parts, or about 0.2-0.4 parts, or about 0.25 parts triethanolamine. To prepare a lotion comprising an oil-in-water emulsion, a heated oil phase comprising emulsifying wax, fatty acid, oil and vitamin are gradually added to a vigorously stirring aqueous phase comprising ABL solution and hyaluronic acid.

As another example, to prepare a cream, about 60-75 parts, or about 65-70 parts, or about 67.5 parts (parts refer to grams for every 100 grams of final formulation) of ABL solution (an aqueous dispersion of silver particles from ABL Manufacturing LLC) is combined with about 7-15 parts, or about 8-12 parts, or about 10 parts of emulsifying wax, and about 8-16 parts or about 10-14 parts or about 12 parts of an oil such as coconut oil, and about 4-12 parts, or about 6-10 parts, or about 8 parts of fatty acid such as stearic acid, and about 0.5-2 parts, or about 1 part of a vitamin such as vitamin E, and a pH controlling agent as needed, for example, about 0.1-1 parts, or about 0.2-0.8 parts, or about 0.5 parts triethanolamine. To prepare a cream comprising an oil-in-water emulsion, a heated oil phase comprising emulsifying wax, fatty acid, oil and vitamin are gradually added to a vigorously stirring aqueous phase comprising ABL solution and hyaluronic acid.

Emulsions containing silver particles may be prepared in analogy to the methods disclosed in the references identified herein, but using an aqueous colloidal silver in lieu or, or in addition to, the aqueous phase disclosed in those references.

In various embodiments, the aqueous particulate silver compositions used to prepare the compositions of the present disclosure have silver particles at a concentration of 5-50 ppm, or at 10-40 ppm, or at 15-30 ppm, or at 20-25 ppm (parts per million) in the water.

In various embodiments, the present disclosure provides colloidal silver particles as disclosed herein may be incorporated into the formulations, preparations, compositions and the like that are disclosed in the following PCT and US patent documents. For example, as appropriate, the present invention provides that an aqueous dispersion of colloidal silver particles as disclosed herein may be used in lieu of some or all of the aqueous component(s) in any of the formulations described and/or claimed in the following publications. Each of these publications is incorporated herein by reference: WO14136993 directed to a skin care cosmetic having an antipollution property that can protect the skin from a variety of external irritants including UV rays as well as atmospheric pollutants and acidic liquids. WO15098433 directed to an oil-in-water emulsified sunscreen cosmetic. WO15052804 directed to formulations that contain a low-stringiness thickener such as a polyacrylic acid or a salt thereof. WO15045167 directed to a cosmetic that has excellent glossiness directly after application, which does not exhibit shininess even when sebum emerges with the passage of time, and that causes pores to be less noticeable. This cosmetic is characterized by comprising coated particles (a) in which a flaky substrate powder surface is coated with silicone elastomer particles or silicone elastomer/silicone resin composite particles and an oil component (b) that contains a volatile silicone oil; and by the refraction index of the oil component as a whole being 1.39-1.43. WO14199936 directed to a hair treatment composition that can effectively remove polyvalent metal ions such as calcium ion without using any chelating agent, where the hair treatment composition contains a microemulsion of amodimethicone. WO14196602 directed to a fragrance-containing capsule having a core substance comprising a specified fragrance and a wall material formed from one or more polymers selected from poly(alkyl(meth)acrylates) and polystyrene. WO14174868 directed to an aqueous composition in which a vehicle and drops of oil are present together in stable fashion, and personal care products formed therefrom. WO14171238 directed to a cleansing composition for a pump foamer, having good foam qualities and excellent low-temperature stability, comprising (a) 2-5 mass percent of ionic surfactant(s), and (b) 20-60 mass percent of polyhydric alcohols containing propylene glycol, characterized in that: in the ionic surfactant(s) (a), the content of higher fatty acid soap(s) having 5 to 25 carbon atoms amounts to 90 mass percent or more; and the amount of propylene glycol contained in the polyhydric alcohols (b) is less than 20 mass percent relative to the whole composition. WO14136886 directed to a water-in-oil emulsion cosmetic composition which is capable of remaining stable even in cases where a polar oil is blended therein, having 0.1-2 percent by mass of an organic modified clay mineral; 0.1-2 percent by mass of a hydrophobic silica; 2-5 percent by mass of a silicone surfactant; an oil component wherein 10-50 percent by mass of the total oil component is a non-polar hydrocarbon oil; and 20-60 percent by mass of an aqueous phase component. WO14129240 directed to an emulsion-type eyelash cosmetic (mascara) which can minimize the clogging of a comb without lowering the curling power, characterized by containing (a) 20 to 30 mass percent of an alkyl acrylate copolymer emulsion, (b) 3 to 6 mass percent of a moisturizing agent and (c) 0.1 to 0.4 mass percent of a polyacrylic acid salt. WO13132878 directed to an oil-in-water emulsion composition that is high in the moisturizing effect, characterized by comprising (a) hyaluronic acid or a salt thereof, (b) ammonium acryloyldimethyltaurate/beheneth-25 methacrylate crosspolymer, (c) water-holding oil, (d) glycerin, and (e) ethanol. WO14084099 directed to an external preparation for the skin, which is characterized by containing silver-supported tricalcium phosphate, alum and zinc oxide, where silver-supported tricalcium phosphate serves as a deodorant and alum serves as an antiperspirant, the preparation further containing colloidal silver particles as disclosed herein. WO14077334 directed to formulations that contain phenyl ethyl cinnamate, which inhibits excessive melanin production in the skin, and a whitening agent comprising the same. WO14077189 directed to a water-in-oil emulsion sunscreen cosmetic that has a strong ultraviolet protection effect, characterized by containing hydrophobicized silica-coated zinc oxide microparticles, a volatile hydrocarbon oil, and volatile dimethicone; and the sum of the volatile hydrocarbon oil and volatile dimethicone being 3-45 mass percent relative to the total amount of the sunscreen cosmetic. WO14069173 directed to a sunscreen cosmetic characterized by comprising an ultraviolet-ray-blocking agent; a volatile oily material; cetyl dimethicone copolyol; an (acrylate/stearyl acrylate/dimethicone methacrylate) copolymer; and an organic modified clay mineral. WO14069400 directed to an organosiloxane derivative composition which can cause the stable gelification of small amounts of oils, and which may be used in personal care products. WO14069403 directed to a water-in-oil emulsion composition characterised by comprising 1-20 mass percent of a polyhydric alcohol fatty acid ester and/or a hydrocarbon; 3-20 mass percent of a transparent non-volatile silicone oil; 0.1-5 mass percent of decyl trisiloxane carboxylic acid zinc, and water, useful in the preparation of personal care products. WO14069388 directed to a hair conditioner composition comprising (a) a cationic surfactant, (b) a higher alcohol, (c) an aromatic acid, (d) a high polymer amino-modified silicone, (e) octyl palmitate or a hydrocarbon oil having a melting point of 35 to 53 degrees C., and (f) water. WO14058048 directed to a makeup base cosmetic for skin which comprises a water-containing aqueous phase as a continuous phase and contains a vinyl acetate polymer, a polyhydric alcohol, and a hydrophilic non-ionic surfactant, where the vinyl acetate polymer is present at a ratio of 0.5-7 mass percent relative to the total weight of the cosmetic and dispersed as particles in the aqueous phase; the amount of the polyhydric alcohol is 0.5-5.5 parts by mass per part by mass of the vinyl acetate polymer; and the hydrophilic non-ionic surfactant is present at a ratio of 1-5 mass percent relative to the total weight of the cosmetic. WO14058060 directed to cosmetic formulations used in a method including applying a cosmetic material to skin, a step for pasting the base material film surface of a thin film to skin, and a step for eliminating the support body of the pasted thin film, and is characterized by the thin film comprising a support body and a base material film having a thickness of 10-500 nm. WO14050487 directed to a liquid antiperspirant composition having an excellent sensation of coolness and excellent stability, comprising menthol or a derivative thereof; a di-long-chain-type cationic surfactant; zinc paraphenolsulfonate; ethanol; and a clay mineral. US2015202137 directed to a water-in-oil emulsion cosmetic comprising 0.5 to 10 mass percent of a sterol derivative, a volatile oil having low compatibility with the sterol derivative, an emulsifying agent, and 60 to 90 mass percent of an aqueous component. US2014004210 directed to formulations comprising rosemary extract having a hyaluronidase inhibitory activity, and retinol acetate, which can enhance the hyaluronidase inhibitory activity of rosemary extract. WO13146891 directed to formulations that comprise a subcutaneous fat accumulation inhibitor which comprises at least one component selected from the group consisting of a pine extract, a saffron extract, a cinchona extract and a comfrey extract. WO13146797 directed to preparations that have heparan sulfate production promotion ability and comprise a mixture of an extract of the Madonna lily (*Lilium candidum*) and glucosamine. WO13147012 directed to compositions that include titanium oxide particles which are each composed of rod-shaped titanium oxide primary particles that are gathered into a three-dimensionally radial form and which have particle diameters of 0.5 to 50 mum. WO13136890 directed to an external preparation for the skin comprising silver-supporting antibacterial tricalcium phosphate and a polypropylene glycol having a number average molecular weight of 700-4,000, a copolymer of a polypropylene glycol having a number average molecular weight of 700-4,000 and a polybutylene glycol, or a derivative of a polypropylene glycol having a number average molecular weight of 700-4,000. WO13136616 directed to a water-in-oil emulsion composition which contains 70-98 percent by mass of an aqueous component, with the average emulsion particle diameter of the internal water phase being 10-100 mum, and further comprising 3,7,11,15-tetramethyl-1,2,3-hexadecane triol, diglyceryl diisostearate, a polyoxyethylene-methyl polysiloxane copolymer, an aqueous component, and an oil component. WO13128736 directed to a composition which can be used daily, for inhibiting deterioration in skin condition, the composition containing one or more types of compounds selected from D-methionine, and a derivative and/or a salt thereof, and where the composition may be an external skin preparation, a cosmetic, a wrinkle inhibitor, or a drug for skin diseases. US2014343169 directed to an oil-in-water emulsified skin cosmetic comprising acetylated hyaluronic acid, a specific polymethacryloyloxyethyl phosphorylcholine derivative, non-emulsifying cross-linked silicone, glycerin, polyvinyl alcohol, an acrylamide type thickener, and an oil component. WO13118836 directed to an oil-in-water-type emulsion skin cleanser which has high cleansing performance, which comprises (a) 45 to 70 mass percent of an oily component, (b) 10 to 30 mass percent of a polyoxyethylene monofatty acid glyceryl having an HLB value of 8 to 14, (c) 10 to 45 mass percent of water and (d) 0.01 to 1 mass percent of a thickening agent and has the form of an emulsion or a cream. US2014357721 directed to a redispersible powder-dispersed cosmetic which has a clear supernatant when unused, comprising (A) succinic acid and/or a salt thereof, (B) bentonite and (C) a hydrophilic surfactant. WO13115099 directed to a water-in-oil emulsion makeup cosmetic comprising (A) 0.1 to 10 mass percent of a carboxylic acid-modified silicone having a molecular weight of 800 or lower and including a specific structure, (B) 0.1 to 20 mass percent of a non-volatile oil, (C) 1 to 50 mass percent of a volatile oil, and (D) 2 to 95 mass percent of a powder component. US2014356401 directed to a liquid cosmetic which minimizes stickiness or stiffness caused by the incorporation of a large amount of a moisturizing agent and comprising 10-40 percent by mass of a moisturizing agent, 0.01 to 3 percent by mass of an oil, 0.01-5 percent by mass of a hydrophilic surfactant, and 0.001-0.3 percent by mass polyacrylic acid or a metal salt thereof. US2014348765 directed to a water-in-oil emulsified skin cosmetic comprising water at 5-50 wt percent, ethanol at 1-20 wt percent, volatile oil at 2-50 wt percent, and a carboxy decyl trisiloxane at 0.1-5 wt percent. WO13099378 directed to an extract from the plant *Peucedanum japonicum* Thunb. and having collagen production promoting action, and cosmetic formulations that contain this extract. US2014343170 directed to a corona-core microgel emulsifying agent composed of a copolymer obtained by polymerizing polyethylene oxide macromonomers, hydrophobic monomers, and cross-linking monomers under specific conditions as well as an oil-in-water emulsified composition using the emulsifying agent for emulsification, and cosmetic formulations containing the agent. US2015005396 directed to an oil-in-water emulsion composition which is characterized by containing (A) a non-emulsifying cross-linked polymethyl siloxane, which contains (a1) a dimethicone crosspolymer and (a2) a non-emulsifying cross-linked polymethyl siloxane other than a dimethicone crosspolymer; (B) an associative thickener; (C) a polyether-modified silicone; (D) a silicone oil; and (E) water. US2014323591 directed to a water-based skin cosmetic comprising a thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein the microgel is obtained by radically polymerizing dimethylacrylamide and 2-acrylamido-2 methylpropane sulfonic acid under the conditions in which a single phase microemulsion or fine W/O emulsion is formed by using a surfactant. WO13077072 directed to an oxidation hair dye which comprises a first agent containing an alkaline agent and a second agent containing an oxidizing agent, said first and second agents characterized by, immediately after mixing the first agent with the second agent provides a composition containing a bicontinuous microemulsion phase or a lamellar liquid crystal phase. US2015157546 directed to an oil-in-water type emulsified sunscreen cosmetic which contains (a) 0.1 to 5.0 mass percent of an organosiloxane derivative, (b) 0.1 to 5.0 mass percent of poly(ethylene glycol) stearate, (c) 10.0 to 25.0 mass percent of an ultraviolet radiation absorber and (d) a higher alcohol. US2014255323 directed to an organic UV absorber-free, oil-in-water emulsion sunscreen cosmetic that includes: (A) zinc oxide and/or titanium dioxide hydrophobized with octyltriethoxysilane and/or dimethylpolysiloxane; (B) a liquid higher fatty acid; (C) a silicone or a sugar ester of a structure containing a carboxyl group; (D) a non-ionic surfactant; (E) sodium carboxymethyl cellulose; and (F) water. WO13061712 directed to an O/W emulsion composition having fine emulsion particle diameters that is provided by a method using a higher aliphatic alcohol and an anionic surfactant that forms an alpha-gel in water. US2014235732 directed to an oil-in-water emulsion cosmetic comprising: (A) 0.1-5 mass percent of hydrogenated polyisobutene with a number average molecular weight of 2000 to 3000, (B) 0.1 to less than 1 mass percent of higher alcohol, (C) 1 to 25 mass percent of an oil component, (D) 0.3-5 mass percent of surfactant, (E) 0.05 to 5 mass percent of water-soluble thickener, and (F) an aqueous component, wherein the blending quantity of nonpolar oil is 30 percent or lower of the total amount of component (C). US2014255527 directed to a skin care composition comprising at least one of lavender oil and eucalyptus oil, in addition to an alkylene oxide derivative. WO13047204 directed to a translucent oil-in-water emulsion cosmetic containing 0.01-1 mass percent of a di-long chain cationic surfactant (A), 0.01-2 mass percent of a non-ionic surfactant (B) having a sterol backbone with an HLB of 10-18, 0.01-1 mass percent of an oil (C) that is liquid at room temperature, 0.1-10 mass percent of a specific alkylene oxide derivative (D) (for example, POE(14) POP(7) dimethyl ether or the like), 0.1-20 mass percent of a C1-3 monohydric lower alcohol (E), and water (F), [component (C)/component (A)+component (B)]=0.60 or lower (mass ratio). The translucent oil-in-water emulsion cosmetic may also contain menthol and/or camphor. WO13047196 directed to a formulation for improving silicone elastomer dispersibility (stability), which can be applied to a broad range of oil-in-water emulsion bases, comprising (a) a water-soluble thickener having a hydrophobic group; (b) a non-ionic surfactant having an HLB of 14 or higher; (c) a polyether modified silicone having an HLB of 3-5; and (d) a non-emulsifying crosslinked silicone. WO13038861 directed to a transparent to semi-transparent liquid cosmetic material which contains (a) 0.01 to 3 mass percent of an oil component and (b) a hydrophilic surfactant selected from among a polyoxyethylene hardened castor oil and a polyoxyethylene phytosterol and which has an L value of 60 or higher, wherein isostearyl alcohol accounts for 60 mass percent or more of the oil component (a), and optionally (c) a lipophilic surfactant selected from among polyglyceryl diisostearate, sorbitan sesquiisostearate and sorbitan sesquioleate. WO13031327 directed to an oil-in-water emulsion cosmetic material for skin which comprises glyceryl tricaprylate, monostearic acid polyethylene glycol adduct, a microgel and water. US2013344013 directed to a water-in-oil emulsified sunscreen cosmetic comprising ultraviolet absorbent, silicone backbone powder, methyl polymethacrylate powder, hydrophobicized platelike powder, surfactant, oil and water. US2014205552 directed to a water-in-oil emulsified sunscreen cosmetic characteristically comprising hydrophobicized zinc oxide and/or hydrophobicized titanium dioxide, lipophilic nonionic surfactant, one or more components selected from di(phytosteryl/2-octyldodecyl)N-lauroyl-L-glutamate phytosteryl macadamiate and cholesteryl macadamiate, volatile silicone oil and/or hydrocarbon oil, and water. US2014186281 directed to a water-in-oil-type skin-whitening cosmetic comprising an alkoxysalicylic acid or a salt thereof, an organic modified clay mineral, and a liquid fatty acid. US2014219939 directed to a liquid skin-conditioning composition comprising tranexarnic acid and derivatives thereof and carboxymethylcellulose as a thickener. US2014134255 directed to an oil-in-water emulsion cosmetic having excellent in emulsion stability, comprising (a) to (d): (a) one or more amphipathic substances selected from (a1) to (a3): (a1) an amphipathic protein, (a2) a copolymer of 2-acrylamido-2methylpropane sulfonic acid or a salt thereof and vinylpyrrolidone, (a3) a microgel, (b) particles with the average particle size of less than 500 nm, (c) an oil component, and (d) an aqueous component. WO13008595 directed to an oil-in-water-type external preparation for the skin, comprising (a) a high-molecular-weight polyethylene glycol, (b) a higher alcohol, (c) sodium N-stearoyl-N-methyltaurine in an amount of less than 2.0 mass percent, and (d) a nonionic surfactant. WO12172622 directed to a solid water-in-oil-type emulsion cosmetic comprising a volatile linear dimethylsilicone tetramer, a volatile linear dimethylsilicone pentamer, a solid wax and/or an oil-gelling agent, water, a lipophilic surfactant and a powder. US2014105840 directed to a solid cosmetic for lips comprising (a) 5 to 30 mass percent of hydrogenated polyisobutene, (b) 30 to 70 mass percent of one or more kinds of methyl phenyl silicones that separate from (a) when mixed therewith at 25 degrees centigrade, (c) 0.5 to 15 mass percent of oil that separates from both (a) and (b) when mixed therewith at 25 degrees centigrade, and (d) 4 to 12 mass percent of wax. US2014086864 directed to a shampoo composition comprising: (i) an anionic surfactant which is a taurine-derivative surfactant; (ii) an amphoteric surfactant which is an alkylamide betaine surfactant; (iii) a cationic conditioning polymer; and (iv) 0.01 to 1 mass percent of a quaternary ammonium group-containing silylated urethane polymer. WO12161215 directed to a conditioner composition containing a (i) cationic surfactant, (ii) a higher fatty alcohol, and (iii) 0.01-1 percent by mass of a quaternary-ammonium-group-containing silylated urethane polymer and further characterized in that the cationic surfactant (i) comprises the following: (a) an imidazoline quaternary ammonium salt having a specific structure or a long-chain-dialkyl quaternary ammonium salt having a specific structure; and (b) a long-chain-monoalkyl quaternary ammonium salt having a specific structure. WO12157694 directed to an oil-in-water-type emulsion cosmetic comprising an aqueous phase, an oily phase dispersed in the aqueous phase, and a powder dispersed in the oily phase, and is characterized in that the oily phase contains a silicone oil, a volatile hydrocarbon oil, an organic ultraviolet ray absorber, and a side-chain-type amino-modified silicone. WO12157587 directed to an anti-wrinkle composition comprising a matrix metalloproteinase (MMP) inhibitor and/or laminin 5 production promoter, as well as an anti-wrinkle agent, each of which comprises 1-piperidine propionate and/or a salt thereof. US2014066358 directed to a translucent fragrance composition containing a large amount of perfume, comprising (a) silicone oil and (b) alpha-olefin oligomer that is a hydrogenated trimer, tetramer, pentamer, and/or hexamer of alpha-olefin having 4 to 12 carbon atoms, (c) polyether-modified silicone, (d) perfume which is 3 to 30 percent by mass in the composition; (e) lower alcohol having 1 to 4 carbon atoms and (f) water. WO12141255 directed to a skin lightening composition comprising chafuloside B. WO12133825 directed to a hot flash suppressant composition which contains apelin or an apelin receptor agonist; and further comprising at least one of *Rubus buergeri, Kalimeris yomena, Stauntonia hexaphylla, Rubus grayanus, Kalimeris indica, Pasania edulis, Merica rubra, Syzygium jambos, Quercus serrata* and extracts of these plants, as well as a saffron extract, a pine extract, a cinchona extract, a comfrey extract, a Scutellaria extract, a rosemary extract, an apricot seed powder, a gentian extract, a thyme extract, a mint powder, a *Zizyphi fructus* extract, a hop extract, a kiwifruit extract, a roman chamomile extract, an apple extract, a hawthorn extract and a turmeric extract. WO12132603 directed to a skin care composition comprising (A) a silver ion-supporting antibacterial zeolite and (B) one of a polypropylene glycol having a number-average molecular weight of 700-4,000, a copolymer of a polypropylene glycol and a polybutylene glycol, and a derivative of a polypropylene glycol. US2014017191 directed to a water-in-oil emulsion cosmetic that is excellent in the resilient and supple (in other words, firm and tensional) comprising the following (A) to (D): (A) 0.5 to 10 mass percent of hydrogenated polyisobutene (B) an oil containing (b1) (b1) a volatile oil of low compatibility with (A) (C) an emulsifying agent and (D) 60 to 90 mass percent of an aqueous component, wherein the percentage of component (b1) is 45 to 85 percent with respect to component (A) and component (B). US2014018444 directed to a water-in-oil emulsion cosmetic comprising the following (A) to (D): (A) 0.5 to 10 mass percent of bis-diglyceryl polyacyladipate-2 (B) an oil containing (b1) (b1) a volatile oil of low compatibility with (A) (C) an emulsifying agent and (D) 60 to 90 mass percent of an aqueous component, wherein the percentage of component (b1) is 40 to 85 percent with respect to component (A) and component (B). WO12133293 directed to an eyelash cosmetic comprising (a) 0.1 to 35 mass percent of a dextrin (palmitic acid/2-ethylhexanoic acid) ester, (b) 1 to 13 mass percent of a sucrose fatty acid ester, (c) 0.1 to 10 mass percent of a non-ionic surfactant and (d) 0.1 to 13 mass percent of tri(trimethylsiloxy)silylpropylcarbamic acid-pullulan. US2014024724 directed to a film-shaped external preparation comprising a water-soluble cellulose derivative such as hydroxypropyl methylcellulose as a primary component of the film; and also containing hydroxyethyl urea. WO12132951 directed to a cosmetic material for sunscreen comprising (a) an aqueous dispersion of an oil-soluble ultraviolet ray absorber and (b) agar microgel, and optionally containing bis-ethylhexyloxyphenol methoxyphenyl triazine and an organic polymer, methylene bis-benzotriazolyl tetramethylbutylphenol and nonvolatile dimethicone. WO12124436 directed to a skin cosmetic which has an excellent whitening effect and an excellent wrinkle ameliorating effect comprising: (a) one or more kinds of a pyrimidyl pyrazole compounds; and (b) one or more non-emulsifying crosslinked silicone. WO12124766 directed to a concentrated liquid hair cleaning composition comprising 0.1-5 mass percent of a cationic polymer, 40-60 mass percent of an anionic surfactant, and water. US2014010901 directed to a bleomycin hydrolase production promoter composition comprising one or a plurality of ingredients selected from the group consisting of chestnut rose extract, angelica root extract, cork tree bark extract, *Lamium album* extract, rosemary extract, benzenesulfonyl GABA and erythritol. WO12121309 directed to an oil-based solid cosmetic comprising (a) a solid oil component (a microcrystalline wax, a paraffin wax, etc.) in an amount of 2 to 10 percent by mass, (b) an organic modified clay mineral in an amount of 2.5 to 8 percent by mass, (c) a specific polyglycerol-modified silicone (for example, bis-butyldimethicone polyglyceryl-3, etc.) in an amount of 0.3 to 8 percent by mass, (d) a cationic surfactant in an amount of 0.1 to 2 percent by mass, and (e) a branched saturated fatty acid having 14 to 24 carbon atoms in an amount of 0.2 to 7 percent by mass. US2013331468 directed to oil in water emulsions prepared by a process comprising emulsifying, at a temperature of 70 degrees centigrade or higher, an oil phase comprising (A) a mono-branched fatty acid POE (0-60) glycerin ester, (B) a linear higher alcohol having 16 or more carbon atoms capable to form an alpha-gel in water with said (A), and (C) an oil component, and a part of an aqueous phase (a first aqueous phase) comprising (D) water; and the cooling of this emulsified part by mixing with the remaining main aqueous phase (a second aqueous phase) at 10 to 35 degrees centigrade, wherein an aqueous solvent in the emulsified part is 15 mass percent or less. WO12118055 directed to a transparent or translucent oil-in-water emulsified cosmetic containing, (A) 0.1 to 2 mass percent of a di-long-chain cationic surfactant, (B) 0.1 to 2 mass percent of a non-ionic surfactant with an HLB of 10 to 18, (C) 0.01 to 2 mass percent of an oil that is liquid at room temperature (25° C.), (D) 1 to 20 mass percent of a glycol, and (E) water. WO12115247 directed to a stratum corneum peeling accelerator composition comprising a mesotrypsin expression enhancer selected from the group consisting of *Gingko biloba* extract, *Saxifraga stolonifera* extract, *Rosa roxburghii* extract, dipotassium glycyrrhizate, and ectoine. US2013336908 directed to an oil-in-water sunscreen cosmetic composition comprising: (a) an aqueous dispersion of an oil-soluble ultraviolet absorbent; (b) one or two or more of crosslinked polyether-modified silicones and crosslinked alkyl polyether-modified silicones; (c) a low-viscosity silicone oil; and (d) water, optionally with methylene bisbenzotriazolyl tetramethylbutylphenol. WO12101741 directed to compositions containing a tie-2 activator comprising the extracts of the stem branch or seed of sokakushi (*Gleditsia sinensis* Lam.), polygonatum rhizome (*Polygonatum sibiricum* Red.), Angular Solomon's Seal (*Polygonatum officinalle*), the fruit or seed of trichosanthes (*Trichosanthes kirilowii* Maxim), and/or Indian Mulberry (*Morinda officinalis* How.). WO12098765 directed to a makeup cosmetic produced by mixing (A) a hydrophobization coloring material and (B) metallic soap-treated titanium oxide microparticles. WO12090297 directed to a sunscreen cosmetic characterized in containing (a) 0.1-5 mass percent of phenylbenzimidazole sulfonic acid, and (b) N,N, N',N'-tetrax (2-hydroxypropyl) ethylene diamine. WO12090581 directed to an oil-in-water emulsion sunscreen cosmetic comprising (a) to (e). Component (a) is an acrylic acid/alkyl methacrylate copolymer; (b) is a block type alkylene oxide derivative, (c) is a UV absorber; (d) is an oil; and (e) is water. WO12086579 directed to a W/O emulsion type cosmetic which comprises: (A) 0.1-5 mass percent of a polyoxyalkylene/alkyl co-modified silicone; (B) 0.1-5 mass percent of a polyoxyalkylene modified silicone, (C) 0.1-60 mass percent of a powder; (D) 3-50 mass percent of a volatile oil component; (E) 10-35 mass percent of glycerin; and (F) water. WO12081446 directed to an oil-in-water emulsion sunscreen composition which is characterized by being formed from an oil-in-water emulsion that contains (A) an alkyl phosphate salt and (B) an ultraviolet absorbent and has oil globules having a number average particle diameter of less than 130 nm by high-shear processing. WO12077639 directed to an oil-in-water type eyelash cosmetic comprising 1 to 20 mass percent of (a) a pentaerythritol ester having a melting point of 30 to 45 degrees C.; 5 to 35 mass percent of (b) a wax; and 5 to 45 mass percent of (c) a water-soluble coating agent. WO12073928 directed to a W/O emulsion composition comprising (A) plate-shaped particles of an organically modified clay mineral which have a mean thickness of 0.1 micrometres or less and a mean length of 0.5 to 50 micrometres and (B) a branched-chain silicone which is co-modified with both polyoxyalkylene and alkyl; and having a viscosity of 10,000 mPa·s or less. WO12070309 directed to an oil-in-water type emulsified cosmetic for sunscreen comprising components (A) to (F). (A) zinc oxide, (B) volatile oil, (C) higher fatty acid in a liquid state, (D) silicone or sugar ester containing a carboxyl group in the structure, (E) nonionic detergent, and (F) water. US2013189335 directed to an oil-in-water emulsified composition comprising miniaturized emulsified particles formed by means of high pressure emulsification, and further comprising (A) salt type drug (B) hydrophilic nonionic surfactant (C) N-long chain acyl acidic amino acid mono salt (D) two or more types of higher fatty acids and alkali that constitutes higher fatty acid soap (E) higher alcohol (F) oil component (G) water. WO12056959 directed to an oil-in-water type sunscreen cosmetic comprising a polyether-denatured silicone (A), 3-8 mass percent of a filler (B) and an ultraviolet absorber (C), the ultraviolet absorber having an absorptive capacity in the UV-A range. US2013231401 directed to an oil-in-water external skin preparation of comprising (a) an aqueous phase containing resin particles, (b) an oil phase, and (c) a surfactant comprising one or more selected from polyoxyethylene hydrogenated castor oil, silicone-type surfactants, and sulfonic acid-type surfactants. US2014148516 directed to a water-in-oil type emulsified cosmetic comprising: (A) 20 to 30 mass percent of an oil component; (B) a fatty acid ester having an HLB of 5 to 10; (C) a nonionic surfactant having an HLB of 1 to 4; (D) an organic modified clay mineral; and (E) water. WO12046500 directed to an oil-in-water type emulsion composition comprising components (a) to (e) below: (a) an acrylic acid-methacrylic acid alkyl copolymer, (b) a block-type alkylene oxide derivative, (c) a nonionic surfactant, (d) oil, and (e) water. WO12043614 directed to an oil-in-water type emulsion cosmetic comprising: (A) 0.1-10 mass percent of a polyether-denatured silicone having an HLB (Si) of 5-10; (B) 5-50 mass percent inclusive of ethanol; (C) 0.01-3 mass percent of a hydrophilic thickener; (D) 0.1-15 mass percent of a polyol; and (E) a water-soluble whitening agent. US2013142853 directed to a skin cosmetic comprising agar hydrogel particles having an average particle size of 0.2-5 mm. WO12035904 directed to composition comprising an agent for promoting hyaluronic acid production selected from *Dioscorea esculenta* or an extract thereof. US2013121939 directed to a water-in-oil emulsified cosmetic that characteristically comprises (a) isododecane 3.0-30 wt percent (b) dodecamethylcyclohexasiloxane 1.0-10 wt percent (c) alkyl/polyether comodified silicone and (d) one or more ultraviolet absorbents selected from 2-hydroxy-4-methoxybenzophenone and diethylamino hydroxybenzoyl hexyl benzoate. WO12017733 directed to a skin cosmetic for improving skin disorders comprising (A) one or more D-amino acid, derivative and/or salt thereof, (B) hydrogenated phospholipid in which the content of phosphatidylcholine is 50 percent by mass or more, and (C) a water-soluble polyalcohol, preferably glycerin. As mentioned previously, the compositions as disclosed herein may include any of the formulations described and/or claimed in the above-stated patent documents, in addition to silver particles at, e.g., a concentration of 5-50 ppm, or at 10-40 ppm, or at 15-30 ppm, or at 20-25 ppm (parts per million) in the formulation.

Methods of Use

The present invention provides silver particle-containing emulsions and the use thereof. For example, the compositions of the present disclosure may be used for any of pharmaceutical, dermatological or cosmetic purposes.

In one embodiment, the compositions of the present disclosure may be used as skin care compositions. More specifically, the compositions of the present disclosure may be incorporated into bathing products, soaps, antiperspirants; deodorants such as sticks, soft solid, roll on, aerosol, and pump sprays; skin creams; skin care lotions; moisturizers; facial treatments such as wrinkle control or diminishment treatments; exfoliates; body and facial cleansers; bath oils; perfumes; colognes; sachets; sunscreens; mousses; patches; pre-shave and after-shave lotions; shaving soaps; shaving lathers; depilatories; make-ups; color cosmetics; foundations; concealers; blushes; lipsticks; eyeliners; mascaras; oil removers; color cosmetic removers, powders, and kits thereof.

The cosmetic compositions may be utilized according to standard methods for such products, such as by applying them to the human or animal body, e.g. skin or hair, using applicators, brushes, applying by hand, pouring them and/or possibly rubbing or massaging the composition onto or into the body. Removal methods, for example for colour cosmetics are also well known standard methods, including washing, wiping, peeling and the like.

The cosmetic compositions may be used on skin in a conventional manner. An effective amount of the composition for the purpose is applied to the skin. Such effective amounts generally range from about 1 mg/cm to about 3 mg/cm. Application to the skin typically includes working the cosmetic composition into the skin. This method for applying to the skin comprises the steps of contacting the skin with the cosmetic composition in an effective amount and then rubbing the composition into the skin. These steps can be repeated as many times as desired to achieve the desired benefit.

Benefits obtained from using the cosmetic compositions on skin include one or more of the following benefits: skin softness, suppleness, moisturisation, skin feel, and foam generation. In addition, or alternatively, the compositions of the present disclosure may be used to rejuvenate skin, where this term refers to the full or partial reversal of at least one phenotype typical of an aging cell. Skin rejuvenation can include one or more of the following: reducing the appearance of fine lines and wrinkles; reducing deep wrinkles; enhancing skin tone and elasticity; reducing skin blemishes and/or age spots; reducing skin roughness; and producing a younger looking skin.

The compositions of the present disclosure may help soothe, hydrate and rejuvenate the skin. The compositions of the present invention may help to promote natural healing and rejuvenate the skin. The compositions of the present invention may help the skin to feel softer. These are examples of the healing benefits provided by the formulations of the present disclosure. These benefits may be provided by the serums, lotions, creams, ointments and other forms of the emulsions of the present disclosure that contain particulate silver.

Analytical Methods

The analysis of the silver content in the compositions of this invention may be done by atomic absorption (AA), inductively coupled plasma/atomic emission (ICP/AES), or other techniques known to one of ordinary skill in the art to be sensitive to silver in the appropriate concentration range. If the particles of the silver composition are small and uniformly sized (for example, 0.01 micrometers or less), a reasonably accurate assay may be obtained by running the colloid directly by AA or ICP/AES. This is because the sample preparation for AA ionizes essentially all of the silver allowing its ready detection. If the compositions comprise particles as large as 0.2 micrometers, it is preferred to use a digestion procedure. The digestion procedure is not necessarily ideal for silver compositions that may have been manufactured or stored in contact with halides or other anionic species that may react with finely divided silver, or combined with protein or other gelatinous material.

An embodiment of the digestion procedure is as follows: (a) take a 10 ml aliquot of a thoroughly mixed or shaken silver composition to be analyzed, and place it in a clean glass bottle or other container of suitable material (generally, the bottle) with a tight fitting lid. A size of 30-100 ml is preferred; (b) with a micropipette or dropper, add 0.1 ml of nitric acid, reagent grade to the silver composition in the bottle; (c) with the lid of the bottle tightly in place, heat the composition to 80° C. with mild agitation for a time sufficient to dissolve the silver-dissolution is essentially instantaneous; (d) allow the resulting mixture to cool to room temperature with the lid in place. Shake the bottle thoroughly; (e) utilize AA, ICP/MS, or equivalent means to analyze the silver content of the composition. Preferably, one will utilize a freshly prepared standard or standards, preferably prepared according the equipment manufacturer's instructions, with appropriate dilution as needed. When reporting results, one must take into account all dilutions during preparation, including the 1% dilution caused by addition of the nitric acid.

The analysis of the physical and chemical form of the silver in the compositions may be done by time-of-flight secondary ion mass spectrometry (TOF-SIMS). The TOF-SIMS technique is suitably used as a survey tool to identify the composition of unknown samples. It is capable of quantification if the appropriate microanalytical standards are available for calibration. To perform TOF-SIMS analysis, a few drops of a silver-containing composition are evaporated to dryness on a silicon substrate at ambient temperature. The residue is analyzed by TOF-SIMS. A reference silver (II) oxide (AgO) material is analyzed by placing a few particles of the reference powder as received from the vendor on a silicon substrate, and is denoted as the reference. The time-of-flight secondary ion mass spectrometry technique (TOF-SIMS) is based on the principle of bombarding a solid sample with a pulsed, finely focused beam of primary ions, and then analyzing the secondary ions produced from the surface of the sample via a time-of-flight mass spectrograph. This analytical technique is surface sensitive, deriving its information from a layer that extends to approximately 20 to 40 Å below the surface.

Size/Morphology/Composition Analysis may be performed by any of SEM, EDS (EDAX) and TEM. In particular, the silver/water compositions may be dried and placed on an EM grid and examined in an SEM (i.e., Scanning Electron Microscope) and two different TEMs (i.e., Transmission Electron Microscopes). For example, a silver/water composition may be placed onto C-film and examined by a cryo-TEM at a temperature of about −100° C. using a power level of approximately 100 kV. The silver/water composition of the present invention was therefore substantially instantly frozen. As another example, TEM analysis may be performed in the "SAD" mode. As yet another example, an EDAX spectrum (i.e., an Energy Dispersion Spectrum or "EDS") of silver particles taken from silver/water compositions of the present invention may be used to check for metallic contaminants. In one aspect, the colloidal silver particles do not contain gold or platinum.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The present disclosure provides the following exemplary embodiments:

1) A formulation comprising colloidal silver particles and an emulsion phase.
2) The formulation of embodiment 1 in the form of a lotion.
3) The formulation of embodiment 1 in the form of a skin lotion.
4) The formulation of embodiment 1 in the form of a cream.
5) The formulation of embodiment 1 in the form of a skin cream.
6) The formulation of embodiment 1 in the form of an ointment.
7) The formulation of embodiment 1 in the form of a healing ointment.
8) The formulation of embodiment 1 in the form of a serum.
9) The formulation of embodiment 1 in the form of an anti-aging serum.
10) The formulation of embodiment 1 which is a cosmetic formulation.
11) The formulation of embodiment 1 which is a dermatologic formulation.
12) The formulation of embodiment 1 which is a therapeutic formulation.

13) The formulation of embodiment 1, or any of embodiments 2-12, wherein the silver particles range in size from 1 to 100 nanometers.
14) The formulation of embodiment 1, or any of embodiments 2-12, wherein the silver particles comprises a silver core surrounded by a multivalent silver oxide coating comprised of $Ag_4O_4$ molecules, optionally further described by any one or more of embodiments 13 (wherein the silver particles range in size from 1-100 nanometers), embodiment 15 (having a concentration of silver particles of 1-100 ppm), embodiment 16 (wherein the silver is characterized by particle size, and more than 50% of the silver particles have a maximum dimension of less than 0.015 micrometers), and/or embodiment 17 (having a total concentration of silver particles of between about 5 parts per million and 40 parts per million, wherein said silver is in the form of a stable and colorless colloidal suspension of silver particles having an interior of metallic silver and an exterior surface of silver oxide, optionally ionic silver oxide, wherein at least 75% of the silver particles have diameters between 0.005 micrometers and 0.015 micrometers).
15) The formulation of embodiment 1, or any of embodiments 2-12, having a concentration of silver particles of 1-100 ppm, optionally further described by any one or more embodiment 13, embodiment 14, embodiment 16, and/or embodiment 17.
16) The formulation of embodiment 1, or any of embodiments 2-12, wherein the silver is characterized by particle size, and more than 50% of the silver particles have a maximum dimension of less than 0.015 micrometers, optionally further described by any one or more of embodiment 13, embodiment 14, embodiment 15, and/or embodiment 17.
17) The formulation of embodiment 1, or any of embodiments 2-12, having a total concentration of silver particles of between about 5 parts per million and 40 parts per million, wherein said silver is in the form of a stable and colorless colloidal suspension of silver particles having an interior of metallic silver and an exterior surface of silver oxide, optionally ionic silver oxide, wherein at least 75% of the silver particles have diameters between 0.005 micrometers and 0.015 micrometers.
18) The formulation of embodiment 1, or any preceding embodiment, comprising an oil.
19) The formulation of embodiment 1, or any preceding embodiment, comprising an oil selected from coconut oil, hemp seed oil, argan oil, shea butter, sunflower seed oil, neem oil, jojoba oil, and sweet almond oil.
20) The formulation of embodiment 1, or any preceding embodiment, comprising a fatty acid.
21) The formulation of embodiment 1, or any preceding embodiment, comprising a fatty acid selected from C10-C28 fatty acids.
22) The formulation of embodiment 1, or any preceding embodiment, comprising an emulsifying wax.
23) The formulation of embodiment 1, or any preceding embodiment, comprising a surfactant.
24) The formulation of embodiment 1, or any preceding embodiment, comprising hyaluronic acid.
25) The formulation of embodiment 1, or any preceding embodiment, comprising a pH adjusting agent.
26) The formulation of embodiment 1, or any preceding embodiment, comprising a pH adjusting agent selected from ethanolamine, diethanolamine and triethanolamine.
27) The formulation of embodiment 1, or any preceding embodiment, comprising a component that treat, prevents or controls acne.
28) The formulation of embodiment 1, or any preceding embodiment, comprising a component that imparts lubricity to the composition.
29) A method of improving skin comprising administering an effective amount of a formulation according to any of embodiments 1-28 to skin.
30) A method of making an emulsion comprising combining an aqueous phase and an oil phase, where the aqueous phase comprises particulate silver.
31) The method of embodiment 30 wherein the water phase is added to the oil phase to provide a water-in-oil emulsion.
32) The method of embodiment 30 wherein the oil phase is added to the water phase to provide an oil-in-water emulsion.
33) A personal lubricant composition comprising colloidal silver particles, water, and a thickening agent for the water, where the thickening agent is optionally hydroxyl ethyl cellulose.
34) An acne treatment medicament comprising colloidal silver particles, water, an exfoliant optionally selected from salicylic acid and glycolic acid, and an alcohol optionally selected from ethanol, propylene glycol and polyethylene glycol.

In each of the embodiments described herein, including each of the numbered embodiments 1-34) set forth above, any of the formulations may include silver in the +2 (also known as 2+ or Ag (II)) oxidation state. As mentioned previously, it has been surprisingly found that the selection of silver particles comprising silver in the +2 oxidation state affords a superior formulation. Silver particles in the +2 oxidation state may be used in a low concentration that provides desirable benefits for the formulation, e.g., desirable anti-microbial benefits, and this low concentration does not cause undesirable effects or side-reactions that are observed at higher silver concentration. Thus, the present disclosure provides formulations that contain silver particles comprising silver in the +2 oxidation state, the particles being present in the formulation within a stated concentration range having a minimum and maximum concentration, where the minimum concentration is selected from 0.01 ppm, or 0.02 ppm, or 0.03 ppm, or 0.04 ppm, or 0.05 ppm, or 0.06 ppm, or 0.07 ppm, or 0.08 ppm, or 0.09 ppm, or 0.1 ppm, or 0.2 ppm, or 0.3 ppm, or 0.4 ppm, or 0.5 ppm, or 0.6 ppm, or 0.7 ppm, or 0.8 ppm, or 0.9 ppm, or 1 ppm, or 2 ppm, or 3 ppm, or 4 ppm, or 5 ppm, or 6 ppm, or 7 ppm, or 8 ppm, or 9 ppm, or 10 ppm, and the maximum concentration is selected from 1,000 ppm, or 500 ppm, or 400 ppm, or 300 ppm, or 200 ppm, or 100 ppm, or 90 ppm, or 80 ppm, or 70 ppm, or 60 ppm, 50 ppm, or 40 ppm, or 30 ppm, or 25 ppm, or 20 ppm, or 15 ppm, or 10 ppm. Exemplary silver particle concentrations of 1-100 ppm, or 0.5-500 ppm, or 0.1-1,000 ppm, or less than 20 ppm, or less than 50 ppm, or 10-35 ppm are provided by the present invention, as well as concentrations within 1-100 ppm as mentioned previously. A benefit of using silver (II) at low concentration includes providing a product with a longer shelf life, e.g., providing a product that retains the desired performance benefit for a longer period of time, or providing a product that retains its consistency for a longer period of time, or providing a product that retains its original color for a longer period of time, since unwanted oxidation reactions that can shorten shelf life and/or damage the consistency of the product, and/or cause discoloration, are reduced. For example, the formulation may have at least about 10 ppm silver particles in order to provide good antimicrobial effectiveness but less than about 32 ppm silver particles in order to avoid discoloration of the formulation. Consistency in coloration and/or rheology over time may be measured while the formulation sits at room temperature, for example about 23° C., for a period of time, for example, 1 day, 2 days, 3 days, 4 days, 5 days, 6 days, 1 week, 2 weeks, 3 weeks, 4 weeks, 1 month, 2 months, 3 months, 4 months, 5 months or 6 months. Coloration and rheology may also be evaluated relative to target values. For example, if a white product is desired, and the silver concentration is too high, then a grey or yellowish product may result, indicating that too high of a concentration of silver is present in the formulation. In one embodiment, the silver particles used in the present formulations do not include any substantial amount of silver in the +1 oxidation state, but only has silver in the silver metal or +2 oxidation state, or if silver in the +1 oxidation state is present, it is present in a minor amount, i.e., less than the amount of silver present in the +2 oxidation state. Optionally, the particles contain a thin multivalent silver oxide coating, built of numerous $Ag_4O_4$ molecules which surround a metallic nano-sized silver core. With the $Ag_4O_4$ coating, the nano silver particle may become attracted to the surrounding water molecules, and as such, becomes part of the structure of the water. Within optional embodiments of the invention these particles can range in size from 1-100 nanometers, or from 1-10 nanometers, or from 5-7 nanometers. Moreover, within preferred embodiments the particles are surrounded by a multivalent silver oxide coating comprised of $Ag_4O_4$ molecules.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

In the foregoing description, certain specific details are set forth to provide a thorough understanding of various disclosed embodiments. However, one skilled in the relevant art will recognize that embodiments may be practiced without one or more of these specific details, or with other methods, components, materials, etc.

The Examples and preparations provided below further illustrate and exemplify the formulations of the present invention and methods of preparing such formulations. It is to be understood that the scope of the present invention is not limited in any way by the scope of the following Examples and preparations. In the following Examples, the starting materials and various reactants utilized or referenced in the examples may be obtained from commercial sources, or are readily prepared from commercially available organic compounds, using methods well-known to one skilled in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

EXAMPLES

General Procedures: The efficacy of the colloidal silver particles as a preservative for the lotions and creams of the present disclosure was tested according to the procedure described in the United States Pharmacopeia (USP 36) National Formulary, General Chapter 51, as the Antimicrobial Effectiveness Test (AET). This test is sometimes referred to as preservative challenge testing. The AET method challenges preserved products with a variety of microorganisms representing a spectrum of manufacturing, nosocomial and household contaminants, where such microorganisms may include gram-negative and gram-positive bacteria, yeast and mold species.

The AET method was used herein to challenge (inoculate) the lotions and creams of the present disclosure with 6 different microorganisms: *Candida albicans* (ATCC 10231, a yeast, which is a form of fungus); *Escherichia coli* (ATCC 8739, a bacterium also known as "*E. coli*"); *Staphylococcus aureus* (ATCC 6538, a bacterium also known as "Staph"); *Pseudomonas aeruginosa* (ATCC 9027, a bacterium); *Staphylococcus aureus* subsp. *aureus* Rosenbach (ATCC 43300, a bacterium, also known as Methicillin Resistant *Staphylococcus aureus* (MRSA)); and *Enterococcus faecalis* (ATCC 51299, also known as Vanomycin Resistant *Enterococcus* (VRE)).

A sufficient volume of test product (typically 10 ml) is distributed into each of 5 separate containers, and each container is inoculated with a separate test microorganism (mentioned above). The initial concentration of viable microorganisms in the test product is determined by standard dilution and plate count methods. Inoculated test products are incubated at 22.5±2.5° C. and sampled to determine microorganism concentration at time intervals. The microorganism concentration at each interval is compared to the initial concentration, and then preservative effectiveness is determined based USP guidelines The results from the AET of the lotion of Example 1 and the cream of Example 2 are provided in Tables 1 (A and B) and 2 (A and B), respectively. In Tables 1 and 2, "Initial" refers to the initial concentration of the microorganism added to the lotion (Table 1) or cream (Table 2) having the corresponding ATCC reference number; "L.R." refers to Log Reduction; "min." refers to minutes; and "k" refers to thousand.

Example 1

Preparation of Cosmetic Lotion Having an Oil-in-Water Emulsion

ASAP10 Silver Solution™ (ABL Manufacturing LLC, American Fork, Utah, USA) is heated to 120° F. with vigorous agitation. Hyaluronic acid is slowly added to the hot silver solution and then the mixture is stirred for about 1 hour until it becomes clear. In a separate container, emulsifying wax and stearic acid are melted together using microwave heating in 30-45 second bursts until a melt is achieved. Coconut oil is then added to the molten mixture with stirring to provide a homogeneous melt. If needed, additional microwave heating may be applied in order to maintain the melt at about 120° F. Vitamin E is then added to the molten mixture with stirring, and additional heating is applied as needed to provide a homogeneous molten oil phase at about 120° F. With both the aqueous and oil mixtures in separate contains at 120° F., the oil mixture is gradually added to the vigorously stirred aqueous solution. The mixture is continually stirred until a homogeneous oil in water emulsion forms; typically 5-10 minutes of additional stirring is needed. This emulsion is a cosmetic lotion according to the present disclosure.

This cosmetic lotion was submitted for preservative challenge testing performed according to the procedure described in the United States Pharmacopeia (USP 36) National Formulary, General Chapter 51, as the Antimicrobial Effectiveness Test (AET). The results are provided in Table 1A (for testing 10 minutes, 60 minutes and 4 hours after inoculation) and Table 1B (for testing 1 day, 7 days and 28 days after inoculation), and show that the silver-containing lotion of the present disclosure has good resistance to microorganism growth.

TABLE 1A

Concentration of ATCC-identified microorganism at predetermined time points after inoculation

| ATCC | Initial | 10 min. | L.R. | 60 min. | L.R. | 240 min. | L.R. |
|---|---|---|---|---|---|---|---|
| 43300 | $5.2 \times 10^5$ | >30k | <1.24 | >30k | <1.24 | >30k | <1.24 |
| 51299 | $8.9 \times 10^5$ | 50 | 4.25 | 12k | 1.87 | 200 | 3.65 |
| 9027 | $7.7 \times 10^5$ | 300 | 3.41 | 300 | 3.41 | 150 | 3.71 |
| 8739 | $6.8 \times 10^5$ | 2500 | 2.43 | 3k | 2.36 | 600 | 3.05 |
| 10231 | $9.9 \times 10^5$ | 30 | 4.52 | 50 | 4.30 | <10 | <5.04 |
| 6538 | $6.3 \times 10^5$ | >30k | <1.32 | >30k | <1.32 | 800 | 2.90 |

TABLE 1B

Concentration of ATCC-identified microorganism at predetermined time points after inoculation

| ATCC | Initial | 1 day | L.R. | 7 days | L.R. | 28 days | L.R. |
|---|---|---|---|---|---|---|---|
| 43300 | $6.1 \times 10^5$ | >30k | <1.31 | <10 | >4.83 | <10 | >4.83 |
| 51299 | $5.8 \times 10^5$ | <10 | >4.81 | <10 | >4.81 | <10 | >4.81 |
| 9027 | $8.2 \times 10^5$ | <10 | >3.96 | <10 | >3.96 | <10 | >3.96 |
| 8739 | $7.3 \times 10^5$ | <10 | >4.91 | <10 | >4.91 | <10 | >4.91 |
| 10231 | $6.1 \times 10^5$ | <10 | >4.83 | <10 | >4.83 | <10 | >4.83 |
| 6538 | $4.2 \times 10^5$ | <10 | >4.67 | <10 | >4.67 | <10 | >4.67 |

Example 2

Preparation of Cosmetic Cream having an Oil-in-Water Emulsion

ASAP10 Silver Solution™ (ABL Manufacturing LLC, American Fork, Utah, USA) is heated to 120° F. with vigorous agitation. Hyaluronic acid is slowly added to the hot silver solution and then the mixture is stirred for about 1 hour until it becomes clear. In a separate container, emulsifying wax and stearic acid are melted together using microwave heating in 30-45 second bursts until a melt is achieved. Coconut oil is then added to the molten mixture with stirring to provide a homogeneous melt. If needed, additional microwave heating may be applied in order to maintain the melt at about 120° F. Vitamin E is then added to the molten mixture with stirring, and additional heating is applied as needed to provide a homogeneous molten oil phase at about 120° F. With both the aqueous and oil mixtures in separate contains at 120° F., the oil mixture is gradually added to the vigorously stirred aqueous solution. The mixture is continually stirred until a homogeneous oil in water emulsion forms; typically 5-10 minutes of additional stirring is needed. This emulsion is a cosmetic lotion according to the present disclosure.

This cosmetic lotion was submitted for preservative challenge testing performed according to the procedure described in the United States Pharmacopeia (USP 36) National Formulary, General Chapter 51, as the Antimicrobial Effectiveness Test (AET). The results are provided in Table 2A (for testing 10 minutes, 60 minutes and 4 hours after inoculation) and Table 2B (for testing 1 day, 7 days and 28 days after inoculation), and show that a silver-containing lotion of the present disclosure has good resistance to microorganism growth.

TABLE 2A

Concentration of ATCC-identified microorganism at predetermined time points after inoculation

| ATCC | Initial | 10 min. | L.R. | 60 min. | L.R. | 240 min. | L.R. |
|---|---|---|---|---|---|---|---|
| 43300 | $5.2 \times 10^5$ | >30k | <1.24 | 25k | 1.32 | 300 | 3.24 |
| 51299 | $8.9 \times 10^5$ | <10 | >5.0 | <10 | >5.0 | <10 | >5.0 |
| 9027 | $7.7 \times 10^5$ | <10 | >4.93 | <10 | >4.93 | <10 | >4.93 |
| 8739 | $6.8 \times 10^5$ | 50 | 4.13 | <10 | >4.88 | 40 | 4.23 |
| 10231 | $9.9 \times 10^5$ | <10 | >5.04 | <10 | >5.04 | <10 | >5.04 |
| 6538 | $6.3 \times 10^5$ | 750 | 2.92 | 100 | 3.80 | <10 | >4.85 |

TABLE 2B

Concentration of ATCC-identified microorganism at predetermined time points after inoculation

| ATCC | Initial | 1 day | L.R. | 7 days | L.R. | 28 days | L.R. |
|---|---|---|---|---|---|---|---|
| 43300 | $6.1 \times 10^5$ | <10 | >4.83 | <10 | >4.83 | <10 | >4.83 |
| 51299 | $5.8 \times 10^5$ | <10 | >4.81 | <10 | >4.81 | <10 | >4.81 |
| 9027 | $8.2 \times 10^5$ | <10 | >3.96 | <10 | >3.96 | <10 | >3.96 |
| 8739 | $7.3 \times 10^5$ | <10 | >4.91 | <10 | >4.91 | <10 | >4.91 |
| 10231 | $6.1 \times 10^5$ | <10 | >4.83 | <10 | >4.83 | <10 | >4.83 |
| 6538 | $4.2 \times 10^5$ | <10 | >4.67 | <10 | >4.67 | <10 | >4.67 |

Example 3

Preparation of Sunscreen having an Oil-in-Water Emulsion

ASAP10 Silver Solution™ (ABL Manufacturing LLC, American Fork, Utah, USA, 60 wt % of the product sunscreen) is heated to 120° F. with vigorous agitation. In a separate container, emulsifying wax (8 wt %) is melted using microwave heating in 30-45 second bursts until a melt is achieved. Coconut oil (2 wt %) is then added to the molten mixture with stirring to provide a homogeneous melt. If needed, additional microwave heating may be applied in order to maintain the melt at about 120° F. Ascorbic acid (0.5 wt %) and glycerin (2 wt %) are then added to the molten mixture with stirring, and additional heating is applied as needed to provide a homogeneous molten oil phase at about 120° F. Zinc oxide (25 wt %) is then stirred into this molten mixture. With both the aqueous and oil mixtures in separate contains at 120° F., the oil mixture is gradually added to the vigorously stirred aqueous solution. The mixture is continually stirred until a homogeneous oil in water emulsion forms; typically 5-10 minutes of additional stirring is needed. This emulsion is a sunscreen according to the present disclosure.

Example 4

Preparation of Personal Lubricant

ASAP10 Silver Solution™ (ABL Manufacturing LLC, American Fork, Utah, USA, 98 wt % of the product lubricant) is combined with 2 wt % of hydroxy ethyl cellulose and with vigorous stirring to provide a viscous composition useful as a personal lubricant.

Example 5

Preparation of Acne Medication

ASAP10 Silver Solution™ (ABL Manufacturing LLC, American Fork, Utah, USA, 50 wt % of the product acne medication) is combined with a mixture of propylene glycol (35 wt %), ethanol (10 wt %), glycolic acid (3 wt %) and salicylic acid (2 wt %) with stirring to provide a composition useful as an acne medication.

Example 6

Preparation of Acne Medication

ASAP10 Silver Solution™ (ABL Manufacturing LLC, American Fork, Utah, USA, 75 wt % of the product acne medication) is combined with a mixture of polyethylene glycol 400 (20 wt %), glycolic acid (3 wt %) and salicylic acid (2 wt %) with stirring to provide a composition useful as an acne medication.

Example 7

Preparation of Acne Medication

ASAP10 Silver Solution™ (ABL Manufacturing LLC, American Fork, Utah, USA, 75.5 wt % of the product acne medication) is combined with a mixture of polyethylene glycol 400 (10 wt %), propylene glycol (10 wt %), salicylic acid (2 wt %), glycolic acid (2 wt %), Carbopol Ultrez 30™ (a cross-linked homopolymer of acrylic acid with thickening properties; 1.5 wt %) and sodium hydroxide (1 wt %) with stirring to provide a composition useful as an acne medication.

Although any methods and materials similar or equivalent to those described herein can also be used in the practice or testing of the present invention, a limited number of the exemplary methods and materials are described herein.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A formulation in a form selected from a lotion and a cream, the formulation comprising colloidal silver particles, hyaluronic acid, coconut oil, octadecaonic acid, glycerin, vitamin E, and an emulsifying wax at a concentration of 3-10 wt % to stabilize an emulsion phase.

2. The formulation of claim 1 which is selected from a cosmetic formulation, a dermatologic formulation, and a therapeutic formulation.

3. The formulation of claim 1 wherein the silver particles range in size from 1-100 nanometers.

4. The formulation of claim 1 wherein the silver is characterized by particle size, and more than 50% of the silver particles have a maximum dimension of less than 0.015 micrometers.

5. The formulation of claim 1 wherein the silver particles comprises a metallic silver core surrounded by a multivalent silver oxide coating comprised of $Ag_4O_4$ molecules.

6. The formulation of claim 1 having a concentration of silver particles of 10-40 ppm.

7. The formulation of claim 1 having a total concentration of silver particles of between about 5 parts per million and 40 parts per million, wherein said silver is in the form of a stable and colorless colloidal suspension of silver particles having an interior of metallic silver and an exterior surface of silver oxide, optionally ionic silver oxide, wherein at least 75% of the silver particles have diameters between 0.005 micrometers and 0.015 micrometers.

8. The formulation of claim 1 comprising a component that treat, prevents or controls acne.

9. The formulation of claim 1 comprising a component that imparts lubricity to the composition.

10. A method of improving skin comprising administering an effective amount of a formulation according to claim 1 to skin.

11. A method of making a formulation of claim 1 comprising combining an aqueous phase and an oil phase, where the aqueous phase comprises particulate silver, to provide an emulsion having from 10 to 40 ppm of silver particles.

12. The method of claim 11 wherein the aqueous phase is added to the oil phase to provide a water-in-oil emulsion.

13. The method of claim 11 wherein the oil phase is added to the aqueous phase to provide an oil-in-water emulsion.

* * * * *